(12) United States Patent
Mackewitz et al.

(10) Patent No.: US 7,049,473 B2
(45) Date of Patent: May 23, 2006

(54) HYDROFORMYLATION

(75) Inventors: Thomas Mackewitz, Römerberg (DE);
Martin Volland, Heidelberg (DE);
Rocco Paciello, Bad Dürkheim (DE);
Ansgar Schäfer, Karlsruhe (DE);
Bernhard Breit, Gundelfingen (DE);
Wolfgang Seiche, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/806,249

(22) Filed: Mar. 23, 2004

(65) Prior Publication Data

US 2004/0199024 A1  Oct. 7, 2004

(30) Foreign Application Priority Data

Mar. 25, 2003 (DE) ................. 103 13 319

(51) Int. Cl.
*C07C 45/50* (2006.01)
*B01J 31/00* (2006.01)

(52) U.S. Cl. ............... 568/454; 502/152; 502/162; 502/166

(58) Field of Classification Search ............... 568/454; 502/152, 162, 166
See application file for complete search history.

(56) References Cited

U.S. PATENT DOCUMENTS

| 4,687,874 A | 8/1987 | Oswald et al. ............... 568/454 |
| 4,786,443 A | 11/1988 | Drent et al. ................. 260/549 |
| 4,940,787 A | 7/1990 | Drent ......................... 536/124 |
| 5,710,344 A * | 1/1998 | Breikss et al. ............... 568/454 |
| 6,521,793 B1 * | 2/2003 | Guram et al. ............... 564/433 |

FOREIGN PATENT DOCUMENTS

WO          80/01690          8/1980

OTHER PUBLICATIONS

Catalysis, Ed. 79, pp. 199-248, Elsevier, Moulijin Ed.
J. Org. Chem. 2000, 65, pp. 6917-6921, Akazome et al.
J. Org. Chem. 1978, 43, pp. 947-949, Newkome et al.
J. Am. CHem. Soc. 2003, 125, 6608-6609, Breit et al.
Unpublished Germany application 103 550 66.6.

* cited by examiner

*Primary Examiner*—Sikarl A. Witherspoon
(74) *Attorney, Agent, or Firm*—Novak Druce & Quigg, LLP

(57) ABSTRACT

The present invention relates to a process for hydroformylating in the presence of a catalyst comprising at least one complex of a metal of transition group VIII with monophosphorus compounds which are capable of dimerizing via noncovalent bonds as ligands, to such catalysts and to their use.

17 Claims, 4 Drawing Sheets

Fig. 1: Crystal structure of [cis-PtCl$_2$(6-DPPon)$_2$]
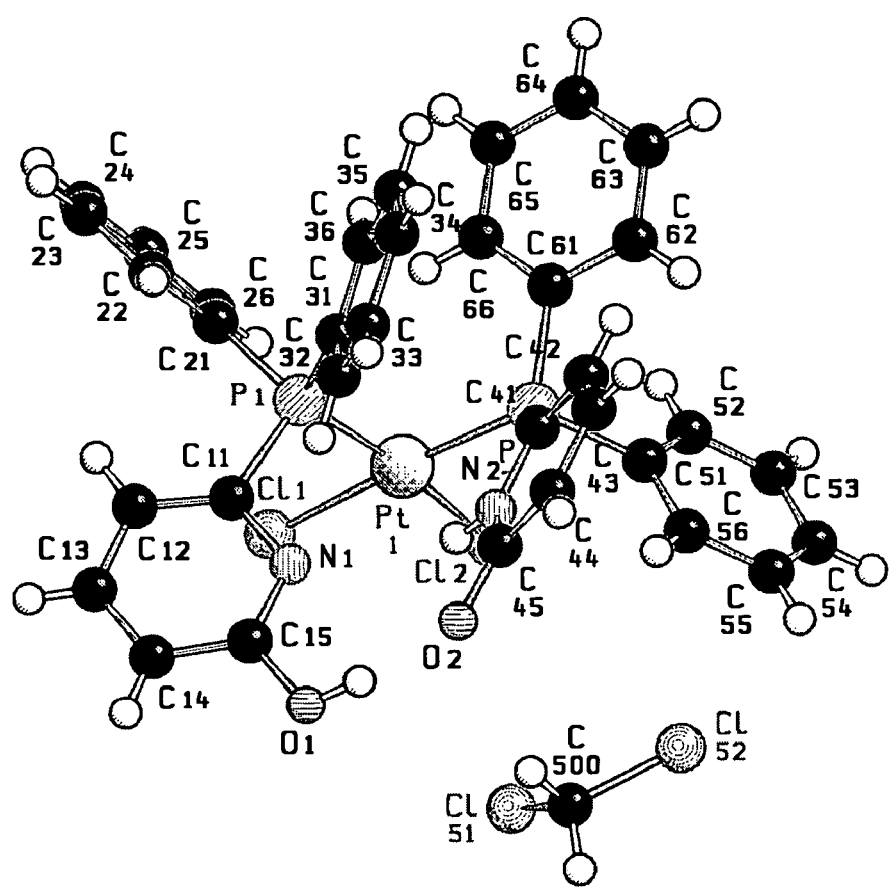

Fig. 2: Crystal structure of [6-DPPAP]
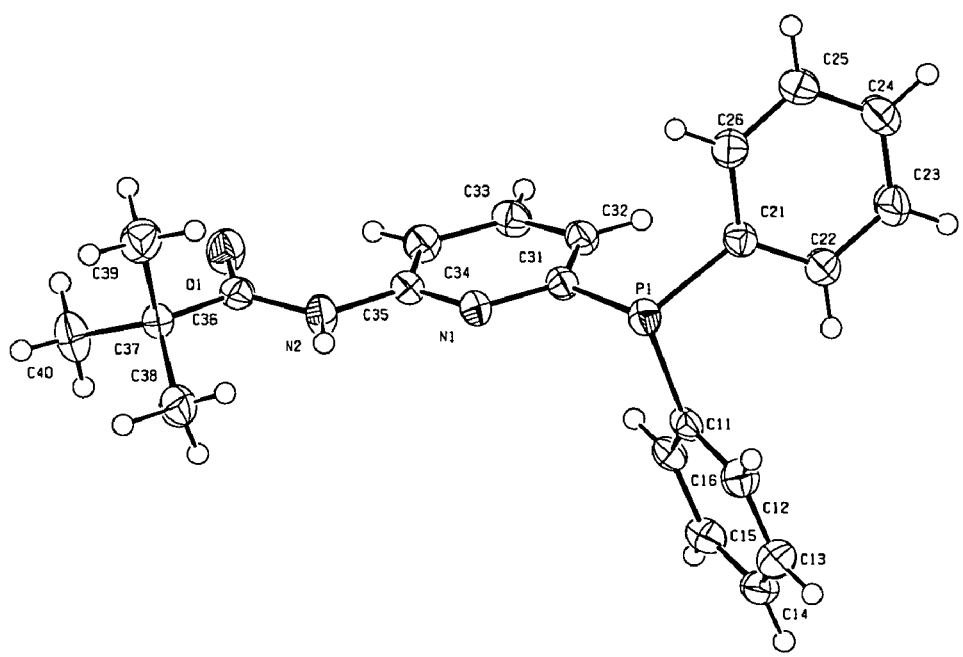

Fig. 3: Crystal structure of [3-DPICon]
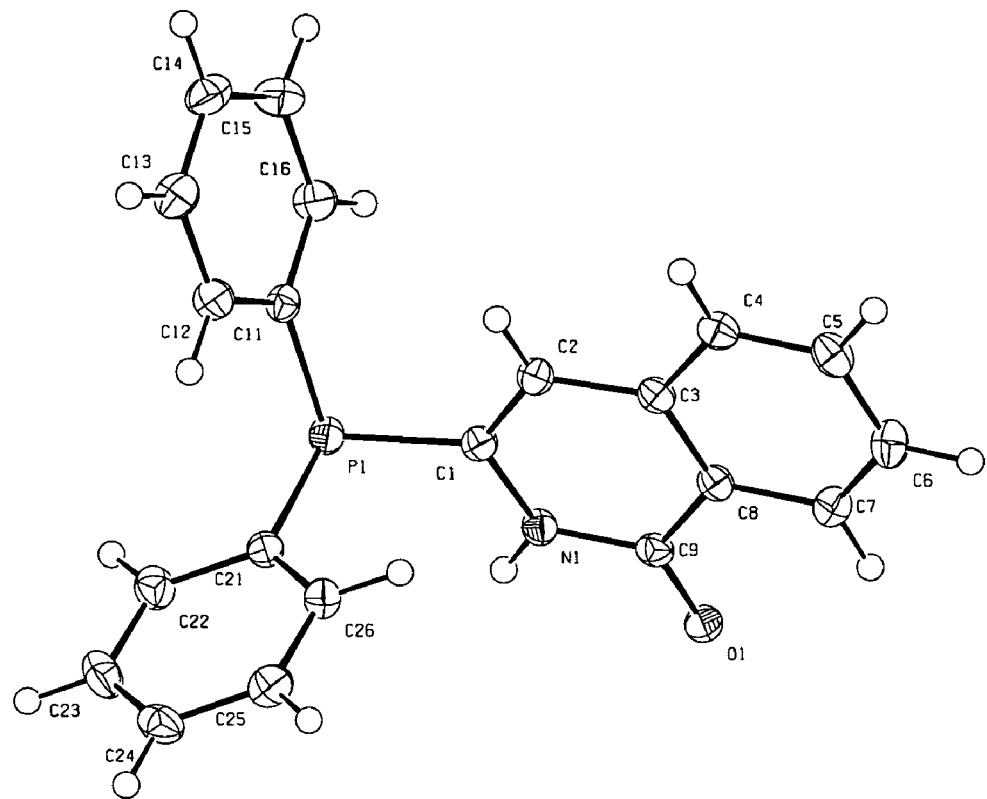

Fig. 4: Crystal structure of [cis-PtCl$_2$(6-DPPAP)(3-DPICon)(H$_2$O)]
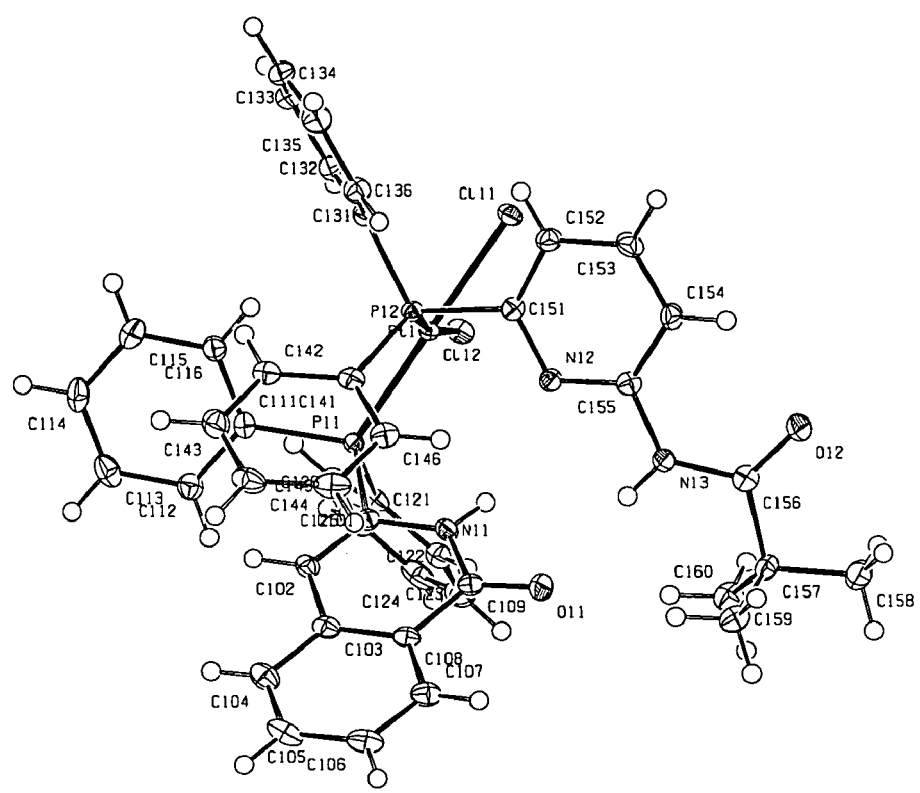

HYDROFORMYLATION

The present invention relates to a process for hydroformylating olefins in the presence of a catalyst comprising at least one complex of a metal of transition group VIII having monophosphorus compounds capable of dimerizing via noncovalent bonds as ligands, to such catalysts and to their use.

The hydroformylation or oxo process is an important large-scale industrial process and serves to prepare aldehydes from olefins, carbon monoxide and hydrogen. These aldehydes may optionally be hydrogenated in the same procedure with hydrogen to give the corresponding oxo alcohols. The reaction itself is strongly exothermic and generally proceeds under elevated pressure and at elevated temperatures in the presence of catalysts. The catalysts used are Co, Rh, Ir, Ru, Pd or Pt compounds or complexes which may be modified with nitrogen or phosphorus ligands to influence the activity and/or selectivity. As a consequence of the possible addition of CO to each of the two carbon atoms of a double bond, the hydroformylation reaction of olefins having more than two carbon atoms may result in the formation of mixtures of isomeric aldehydes. In addition, the use of olefins having at least four carbon atoms may also result in double bond isomerization, i.e. internal double bonds shifting to a terminal position and vice versa.

As a consequence of the significantly greater industrial significance of the α-aldehydes and in particular of the n-aldehydes, there is a drive to optimize hydroformylation catalysts to achieve very high hydroformylation activity with simultaneously very low tendency to form non-α- and especially non-n-aldehydes.

For example, for the preparation of ester plasticizers having good performance properties, there is a demand for plasticizer alcohols having from about 6 to 12 carbon atoms and a certain degree of branching (known as semilinear alcohols) and for corresponding mixtures thereof. These include in particular 2-propylheptanol and alcohol mixtures comprising it. To prepare it, for example, $C_4$-hydrocarbon mixtures which comprise butenes or butenes and butanes may be subjected to a hydroformylation and subsequent aldol condensation. Where hydroformylation catalysts are used which have insufficient n-selectivity, the hydroformylation may readily result in the formation of undesired product aldehydes, which makes the entire process less economically viable.

In low-pressure rhodium hydroformylation, the use of phosphorus ligands to stabilize and/or activate the catalyst metal is known. Suitable phosphorus ligands are, for example, phosphines, phosphinites, phosphonites, phosphites, phosphoramidites, phospholes and phosphabenzenes. The currently most widely used ligands are triarylphosphines, for example triphenylphosphine and sulfonated triphenylphosphine, since these have sufficient stability under the reaction conditions. However, a disadvantage of these ligands is that only very high ligand excesses generally afford satisfactory yields, especially of linear aldehydes.

It is also known that the use of chelate ligands which have two phosphorus groups capable of coordinating has an advantageous effect on the n-selectivity achieved (see Moulijn, van Leeuwen and van Santen, Catalysis, Vol. 79, p. 199–248, Elsevier 1993). However, a disadvantage of the use of chelate ligands is that complicated syntheses are required to prepare them in many cases and/or they can only be obtained in poor yields. There is therefore still a need for readily available ligands for hydroformylation catalysts which enable hydroformylation with high n-selectivity.

In J. Org. Chem. 2000, 65, p. 6917–6921, M. Akazome et al. describe the synthesis, solid state structure and the aggregation behavior of phosphines which bear a 2-pyridone ring. There is no description of use as ligands for transition metal complexes.

In J. Org. Chem. 1978, 43, p. 947–949, G. R. Newkome and D. C. Hager describe a process for preparing pyridyldiphenylphosphines. This document likewise does not describe use as ligands in transition metal catalysts.

U.S. Pat. No. 4,786,443 and U.S. Pat. No. 4,940,787 describe processes for carbonylating acetylenically unsaturated compounds in the presence of a palladium catalyst. Ligands used are phosphines which bear at least one hetaryl radical, for example an optionally substituted pyridyl radical. The use as ligands of phosphines which have at least one group capable of forming noncovalent bonds is not described.

WO 80/01690 describes a rhodium catalyst which includes at least one phosphine ligand in which two aryl groups and, via an alkylene bridge, a heteroatom-containing radical are bonded to the phosphorus atom. The heteroatom-containing radical may be a multitude of different radicals, and some of the radicals mentioned contain carboxamide groups. However, this document does not teach the use of ligands having a functional group which is capable of forming intermolecular noncovalent bonds. For instance, the only example of carboxamide-containing ligands is (N-2-pyrolidinonyl-ethyl)diphenylphosphine, which is not capable of forming intermolecular noncovalent bonds between the amide groups. U.S. Pat. No. 4,687,874 has a comparable disclosure content to WO 80/01690.

A publication, published after the priority date of the present invention, of B. Breit and W. Seiche in J. Am. Chem. Soc. 2003, 125, 6608–6609 describes the dimerization of monodentate ligands via hydrogen bonds to form bidentate donor ligands and their use in hydroformylation catalysts having high regioselectivity.

The unpublished German patent application 103 55 066.6 describes a process for preparing chiral compounds in the presence of a catalyst which comprises at least one transition metal complex having ligands which have functional groups capable of forming intermolecular, noncovalent bonds.

It is an object of the present invention to provide a hydroformylation process which is suitable for hydroformylating 1-olefins with high n-selectivity. In the process, hydroformylation catalysts should preferably be used whose ligands can be prepared readily and in good yields. The catalysts should have a high selectivity in favor of the hydroformylation compared to the hydrogenation, and/or enable a high space-time yield. They should in particular also afford good yields of linear aldehydes with lower ligand excesses compared to the catalyst metal than in the case of the prior art catalysts.

We have found that this object is achieved by the use of monophosphorus ligands which are capable of forming intermolecular noncovalent bonds. Such ligands may in principle dimerize via intermolecular noncovalent bonds and thus form pseudochelate complexes.

The present invention therefore provides a process for hydroformylating compounds which contain at least one ethylenically unsaturated double bond by reacting with carbon monoxide and hydrogen in the presence of a catalyst comprising at least one complex of a metal of transition group VIII of the Periodic Table of the Elements with ligands which each have a phosphorus group and at least one functional group which is capable of forming intermolecular noncovalent bonds, wherein the complex has ligands which are dimerized via intermolecular noncovalent bonds and wherein the distance between the phosphorus atoms of the dimerized ligands is at most 5 Å.

The present invention also relates to catalysts comprising complexes with a metal of transition group VIII of the Periodic Table of the Elements which comprise ligands which have a phosphorus group and at least one functional group capable of forming intermolecular noncovalent bonds.

The invention further provides a process for preparing 2-propylheptanol, which comprises the hydroformylation of butene, an aldol condensation of the hydroformylation products obtained in this way and the subsequent hydrogenation of the condensation products, using a complex of a metal of transition group VIII with the above-described ligands as the hydroformylation catalyst.

It has been found that the use in hydroformylation of monophosphorus ligands (ligands which have only one phosphorus group per molecule) which are capable of forming dimers via intermolecular noncovalent bonds, and in which the distance between the two phosphorus atoms is in a range which is customary for chelate ligands, results in an n-selectivity being achieved which is so high as to otherwise only be achieved with chelate ligands. Ligands having the capability of forming dimers via intermolecular noncovalent bonds are also referred to in the description as pseudochelate ligands.

According to the invention, ligands are used which have a functional group which is capable of forming intermolecular noncovalent bonds. These bonds are preferably hydrogen bonds or ionic bonds, in particular hydrogen bonds. In a preferred embodiment, the functional groups may be groups capable of tautomerizing. The functional groups capable of forming intermolecular noncovalent bonds make the ligands capable of associating, i.e. of forming aggregates in the form of dimers.

In the context of the present invention, a pair of functional groups of two ligands which are capable of forming intermolecular noncovalent bonds is referred to as "complementary functional groups". "Complementary compounds" are ligands/ligand pairs which have mutually complementary functional groups. Such pairs are capable of associating, i.e. of forming aggregates.

The functional groups capable of forming intermolecular noncovalent bonds are preferably selected from hydroxyl, primary, secondary and tertiary amino, thiol, keto, thioketone, imine, carboxylic ester, carboxamide, amidine, urethane, urea, sulfoxide, sulfoximime, sulfonamide and sulfonic ester groups.

These functional groups are preferably self-complementary functional groups, i.e. the noncovalent bonds are formed between two identical functional groups of the ligands used. When there is only one type of ligands which form ligand/ligand pairs, these are referred to as "homodimers". Functional groups which are capable of tautomerizing may each be present in the dimers in the form of identical or different isomers (tautomers). For example, in the case of keto-enol tautomerization, both monophosphorus ligands may be in the keto form, both in the enol form or one in the keto form and one in the enol form.

In a further suitable embodiment, at least two different ligands are used in the process according to the invention and have functional groups capable of forming inter-molecular, noncovalent bonds. In this case, different ligands exclusively or at least partly form the ligand/ligand pairs (known as "hetero-dimers"). The functional groups of the two different ligands which form the noncovalent bond may be identical or different groups. Functional groups which are capable of tautomerizing may each be present in the dimers in the form of the same or as different isomers (tautomers). The molar ratio of the two ligands which form the heterodimer is preferably in the range from 30:1 to 1:30.

The distance between phosphorus atoms of the dimerized ligands is preferably in the range from 2.5 to 4.5 Å, more preferably from 3.5 to 4.2 Å. Especially suitable is a distance between the phosphorus atoms of from 3.6 to 4.1 Å, for example from 3.7 to 4.0 Å.

Suitable methods for determining whether the ligands used are capable of forming dimers include crystal structure analysis, NMR spectroscopy and molecular modeling methods. For the determination, it is generally sufficient to use the ligands in uncomplexed form. This is especially true for molecular modeling methods. It has additionally been found that crystal structure analysis in the solid state and NMR spectroscopy in solution and calculation of the structure for the gas phase generally all achieve reliable forecasts of the behavior of the ligands used under the hydroformylation conditions. For instance, ligands which are capable of forming dimers by the determination methods mentioned generally have properties under hydroformylation conditions as are otherwise customary only for chelate ligands. These include in particular the achievement of high n-selectivity in the hydroformylation of 1-olefins. It has also been found that this high n-selectivity is no longer achieved when the formation of intermolecular noncovalent bonds between the ligands is disrupted in the hydroformylation by adding acids or protic solvents, for example methanol.

In a suitable procedure for determining whether a ligand is suitable for the process according to the invention, a graphic molecular modeling program is initially used to generate all possible hydrogen-bonded dimers of the ligand and its tautomers. These dimer structures are then optimized by quantum chemistry methods. For this purpose, preference is given to using density functional theory (DFT), for example using the functional B-P86 (A. D. Becke, Phys. Rev. A 1988, 38, 3098; J. P. Perdew, Phys. Rev. B 1986, 33, 8822; ibid 1986, 34, 7406(E)) and the basis SV(P) (A. Schäfer, H. Horn, R. Ahlrichs, J. Chem. Phys. 1992, 97, 2571) in the Turbomole program package (R. Ahlrichs, M. Bär, M. Häser, H. Horn, C. Kölmel, Chem. Phys. Lett. 1989, 162, 165; M. v. Arnim, R. Ahlrichs; J. Comput. Chem. 1998, 19, 1746) (obtainable from the University of Karlsruhe). A commercially available suitable molecular modeling package is Gaussian 98 (M. J. Frisch, J. A. Pople et al., Gaussian 98, Revision A.5, Gaussian Inc., Pittsburgh (Pa.) 1998).

Suitable pseudochelate ligands are only those in which the distance between the phosphorus atoms in the calculated dimer structure is less than 5 Å.

For the purpose of illustrating the present invention, the term "alkyl" encompasses straight-chain and branched alkyl groups. These are preferably straight-chain or branched $C_1$–$C_{20}$-alkyl, more preferably $C_1$–$C_{12}$-alkyl, particularly preferably $C_1$–$C_8$-alkyl and very particularly preferably $C_1$–$C_4$-alkyl groups. Examples of alkyl groups are in particular methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The term "alkyl" also encompasses substituted alkyl groups which generally have 1, 2, 3, 4 or 5, preferably 1, 2 or 3 and more preferably 1, substituent(s). These are preferably selected from cycloalkyl, aryl, hetaryl, halogen, $NE^1E^2$, $NE^1E^2E^{3+}$, carboxylate and sulfonate. A preferred perfluoroalkyl group is trifluoromethyl.

In the context of the present invention, the term "alkylene" refers to straight-chain or branched alkanediyl groups having from 1 to 5 carbon atoms.

In the context of the present invention, the term "cycloalkyl" refers to unsubstituted and also substituted cycloalkyl groups, preferably $C_5$–$C_7$–Cycloalkyl groups, such as cyclopentyl, cyclohexyl or cycloheptyl. In the case of substitution, these generally bear 1, 2, 3, 4 or 5, preferably 1, 2 or 3 and more preferably 1, substituent(s). These substituents are preferably selected from alkyl, alkoxy and halogen.

In the context of the present invention, the term "heterocycloalkyl" encompasses saturated, cycloaliphatic groups having generally from 4 to 7, preferably 5 or 6, ring atoms, in which 1 or 2 of the ring carbon atoms are replaced by heteroatoms selected from the elements oxygen, nitrogen and sulfur and which may optionally be substituted, and in the case of substitution, these heterocycloaliphatic groups may bear 1, 2 or 3, preferably 1 or 2, more preferably 1, substituent(s). These substituents are preferably selected from alkyl, aryl, $COOR°$, $COO^-M^+$ and $NE^1E^2$, particular preference is given to alkyl radicals. Examples of such heterocycloaliphatic groups include pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

In the context of the present invention, the term "aryl" refers to substituted and also unsubstituted aryl groups, and is preferably phenyl, tolyl, xylyl, mesityl, naphthyl, fluorenyl, anthracenyl, phenanthrenyl or naphthacenyl, more preferably phenyl or naphthyl, and in the case of substitution, these aryl groups may generally bear 1, 2, 3, 4 or 5, preferably 1, 2 or 3 and more preferably 1, substituent(s) which is/are selected from the groups of alkyl, alkoxy, carboxylate, trifluoromethyl, sulfonate, $NE^1E^2$, alkylene-$NE^1E^2$, nitro, cyano or halogen. A preferred perfluoroaryl group is pentafluorophenyl.

In the context of the present invention, the term "hetaryl" encompasses unsubstituted or substituted, heterocycloaromatic groups, preferably the pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl groups. In the case of substitution, these heterocycloaromatic groups may bear 1, 2 or 3 substituents which are selected from the groups of alkyl, alkoxy, carboxylate, sulfonate, $NE^1E^2$, alkylene-$NE^1E^2$ or halogen.

In the context of this invention, carboxylate and sulfonate are preferably a derivative of a carboxylic acid function or of a sulfonic acid function respectively, in particular a metal carboxylate or sulfonate, a carboxylic ester or sulfonic ester function or a carboxamide or sulfonamide function. These include, for example, the esters with $C_1$–$C_4$-alkanols, such as methanol, ethanol, n-propanol, isopropanol, n-butanol, sec-butanol and tert-butanol.

The above illustrations of the terms "alkyl", "cycloalkyl", "aryl", "heterocycloalkyl" and "hetaryl" apply correspondingly to the terms "alkoxy", "cycloalkoxy", "aryloxy", "heterocycloalkoxy" and "hetaryloxy".

In the context of the present invention, the term "acyl" refers to alkanoyl or aroyl groups having generally from 2 to 11, preferably from 2 to 8, carbon atoms, for example the acetyl, propanoyl, butanoyl, pentanoyl, hexanoyl, heptanoyl, 2-ethylhexanoyl, 2-propylheptanoyl, pivaloyl, benzoyl or naphthoyl groups.

The $NE^1E^2$, $NE^4E^5$ and $NE^7E^8$ groups are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine and iodine, preferably fluorine, chlorine and bromine.

$M^+$ is one cation equivalent, i.e. a monovalent cation or the fraction of a polyvalent cation corresponding to a single positive charge. The $M^+$ cation merely serves as the counterion to neutralize negatively charged substituent groups, such as the $COO^-$ or the sulfonate group, and may in principle be selected arbitrarily. Preference is therefore given to using alkali metal, in particular $Na^+$, $K^+$, $Li^+$ ions, or onium ions such as ammonium, mono-, di-, tri-, tetraalkylammonium, phosphonium, tetraalkylphosphonium or tetraarylphosphonium ions.

The same applies to the anion equivalent $X^-$ which merely serves as the counterion of positively charged substituent groups, such as the ammonium groups, and may be selected arbitrarily among monovalent anions and the fractions of a polyvalent anion corresponding to a single negative charge, and preference is generally given to halide ions $X^-$, in particular chloride and bromide.

The values for x and y are each an integer from 1 to 240, preferably an integer from 3 to 120.

In the context of the present invention, the term "polycyclic compound" encompasses in the widest sense compounds which contain at least two rings, irrespective of how these rings are joined. These may be carbocyclic and/or heterocyclic rings. The rings may be joined via single or double bonds ("multiring compounds"), connected by fusion ("fused ring systems") or bridged ("bridged ring systems", "cage compounds"). Preferred polycyclic compounds are fused ring systems.

Fused ring systems may be aromatic, hydroaromatic and cyclic compounds joined (fused on) by fusing. Fused ring systems consist of two, three or more than three rings. Depending on the type of joining, a distinction is drawn in fused ring systems between ortho-fusing, i.e. each ring has in each case one edge, i.e. two common atoms, with each neighboring ring, and peri-fusing, in which one carbon atom belongs to more than two rings. Among the fused ring systems, preference is given to ortho-fused ring systems.

The ligand/ligand pairs used in accordance with the invention can be schematically illustrated as follows:

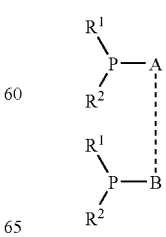

where

A and B are radicals having mutually complementary functional groups, between which there is a noncovalent interaction, $R^1$ and $R^2$ are as defined hereinbelow.

The phosphorus group is preferably selected from groups of the general formula

where $R^1$ and $R^2$ are each independently alkyl, alkoxy, cycloalkyl, cycloalkoxy, heterocycloalkyl, heterocycloalkoxy, aryl, aryloxy, hetaryl or hetaryloxy, or $R^1$ and $R^2$ together with the phosphorus atom to which they are bonded are each a 5- to 8-membered heterocycle which may optionally additionally be singly, doubly or triply fused with cycloalkyl, heterocycloalkyl, aryl or hetaryl, and the heterocycle and, where present, the fused groups may each independently bear one, two, three or four substituents which are selected from alkyl, cycloalkyl, heterocycloalkyl, aryl, hetaryl, $COOR^e$, $COO^-M^+$, $SO_3R^c$, $SO_3^-M^+$, $PO_3(R^c)(R^d)$, $(PO_3)^{2-}(M^+)_2$, $NE^4E^5$, $(NE^4E^5E^6)^+X^-$, $OR^e$, $SR^e$, $(CHR^fCH_2O)_yR^e$, $(CH_2NE^4)_yR^e$, $(CH_2CH_2NE^4)_yR^e$, halogen, nitro, acyl or cyano, where $R^c$ and $R^d$ are each identical or different radicals selected from alkyl, cycloalkyl, aryl and hetaryl, $R^e$, $E^4$, $E^5$, $E^6$ are each identical or different radicals selected from hydrogen, alkyl, cycloalkyl, acyl, aryl and hetaryl, $R^f$ is hydrogen, methyl or ethyl, $M^+$ is one cation equivalent, $X^-$ is one anion equivalent and y is an integer from 1 to 240.

In a first preferred embodiment, $R^1$ and $R^2$ are not joined together. In that case, $R^1$ and $R^2$ are preferably each independently selected from alkyl, cycloalkyl, aryl and hetaryl, as defined at the outset.

Preferably, at least one of the $R^1$ and $R^2$ radicals, and more preferably $R^1$ and $R^2$ are both aryl, in particular both phenyl.

In addition, preference is given to at least one of the $R^1$ and $R^2$ radicals being a pyrrole group bonded to the phosphorus atom via the pyrrolic nitrogen atom. $R^1$ and $R^2$ are preferably both a pyrrole group bonded to the phosphorus atom via the pyrrolic nitrogen atom, and $R^1$ and $R^2$ may be identical or different pyrrole groups.

In the context of the present invention, the term "pyrrole group" refers to a series of unsubstituted or substituted, heterocycloaromatic groups which are structurally derived from the basic pyrrole structure and contain a pyrrolic nitrogen atom in the heterocycle which may be covalently joined to a phosphorus atom. The term "pyrrole group" thus encompasses the unsubstituted or substituted pyrrolyl, imidazolyl, pyrazolyl, indolyl, purinyl, indazolyl, benzotriazolyl, 1,2,3-triazolyl, 1,3,4-triazolyl and carbazolyl groups which, in the case of substitution, may generally bear 1, 2 or 3, preferably 1 or 2, more preferably 1, substituent(s), selected from the groups of alkyl, alkoxy, acyl, carboxylate, sulfonate, $NE^4E^5$, alkylene-$NE^4E^5$ or halogen. Preferred pyrrole groups are 3-($C_1$–$C_4$-alkyl)indolyl groups, such as the 3-methylindolyl group (skatolyl group).

In a further preferred embodiment, $R^1$ and $R^2$ are joined together. In that case, the phosphorus group is preferably a group of the formula

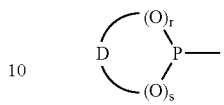

where r and s are each independently 0 or 1, and

D together with the phosphorus atom and the oxygen atom(s) to which it is bonded is a 5- to 8-membered heterocycle which is optionally singly, doubly or triply fused with cycloalkyl, heterocycloalkyl, aryl and/or hetaryl, and the fused groups may each independently bear one, two, three or four subtituents selected from alkyl, alkoxy, halogen, sulfonate, $NE^4E^5$, alkylene-$NE^4E^5$, nitro, cyano and carboxylate, and/or D may have one two or three substituents which are selected from alkyl, alkoxy, optionally substituted cycloalkyl and optionally substituted aryl, and/or D may be interrupted by one, two or three optionally substituted heteroatoms.

The D radical is preferably a $C_2$- to $C_6$-alkylene bridge which is singly or doubly fused with aryl and/or may have a substituent which is selected from alkyl, optionally substituted cycloalkyl and optionally substituted aryl, and/or may be interrupted by an optionally substituted heteroatom.

The fused aryls of the D radicals are preferably benzene or naphthalene. Fused benzene rings are preferably unsubstituted or have 1, 2 or 3, in particular 1 or 2, substituents which are preferably selected from alkyl, alkoxy, halogen, sulfonate, $NE^4E^5$, alkylene-$NE^4E^5$, trifluoromethyl, nitro, carboxylate, alkoxycarbonyl, acyl and cyano. Fused naphthalenes are preferably unsubstituted or have, in the non-fused ring and/or in the fused ring, in each case 1, 2 or 3, in particular 1 or 2, of the substituents mentioned above for the fused benzene rings. In the substituents of the fused aryls, alkyl is preferably $C_1$- to $C_4$-alkyl and in particular methyl, isopropyl and tert-butyl. Alkoxy is preferably $C_1$- to $C_4$-alkoxy and in particular methoxy. Alkoxycarbonyl is preferably $C_1$- to $C_4$-alkoxycarbonyl.

When the $C_2$- to $C_6$-alkylene bridge of the D radical is interrupted by one, two or three optionally substituted heteroatoms, they are preferably selected from O, S and $NR^h$ where $R^h$ is alkyl, cycloalkyl or aryl.

When the $C_2$- to $C_6$-alkylene bridge of the D radical is substituted, it preferably has 1, 2 or 3, in particular 1, substituent(s) which is/are selected from alkyl, cycloalkyl, heterocycloalkyl, aryl and hetaryl, and the cycloalkyl, heterocycloalkyl, aryl and hetaryl substituents may each bear 1, 2 or 3 of the substituents mentioned as suitable for these radicals at the outset.

The D radical is preferably a $C_3$- to $C_6$-alkylene bridge which is fused as described above and/or substituted and/or interrupted by optionally substituted heteroatoms. In particular, the D radical is a $C_3$- to $C_6$-alkylene bridge which is singly or doubly fused with phenyl and/or naphthyl, and the phenyl or naphthyl group may bear 1, 2 or 3 of the aforementioned substituents.

The D radical together with the phosphorus atom and/or the oxygen atom(s) to which it is bonded is preferably a 5- to 8-membered heterocycle in which D is a radical which is selected from the radicals of the formulae II.1 to II.5,

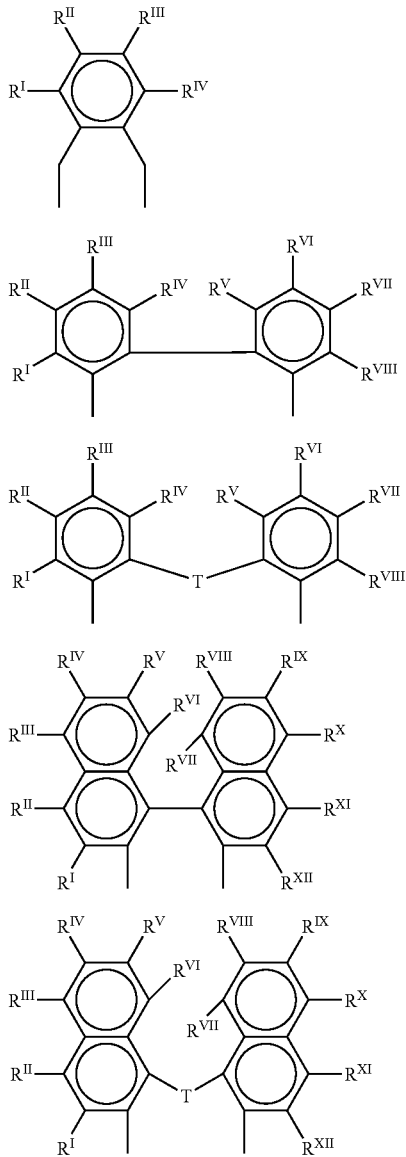

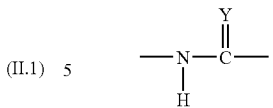

where
T is O, S or NR$^i$ where
R$^i$ is alkyl, cycloalkyl or aryl,
or T is a C$_1$- to C$_3$-alkylene bridge which may have a double bond and/or an alkyl, cycloalkyl or aryl substituent, and the aryl substituent may bear 1, 2 or 3 of the substituents mentioned for aryl,
or T is a C$_2$- to C$_3$-alkylene bridge which is interrupted by O, S or NR$^i$,
R$^I$, R$^{II}$, R$^{III}$, R$^{IV}$, R$^V$, R$^{VI}$, R$^{VII, R VIII}$, R$^{IX}$, R$^X$, R$^{XI}$ and R$^{XII}$ are each independently hydrogen, alkyl, cycloalkyl, aryl, alkoxy, halogen, sulfonate, NE$^4$E$^5$, alkylene-NE$^4$E$^5$, trifluoromethyl, nitro, alkoxycarbonyl or cyano.

At least one of the ligands used in accordance with the invention preferably has a functional group which is capable of tautomerizing and of forming intermolecular noncovalent bonds. It is preferably selected from groups of the formula and the tautomers thereof where Y is O, S or NR$^4$ where R$^4$ is hydrogen, alkyl, cycloalkyl, heterocycloalkyl, aryl or hetaryl.

Factors on which the position of the particular tautomerization equilibrium depends include the Y group and also the substituents capable of tautomerizing. They are illustrated by way of example hereinbelow for keto-enol tautomerization (especially carboxamide-imidocarboxylic acid tautomerization and amidine tautomerization):

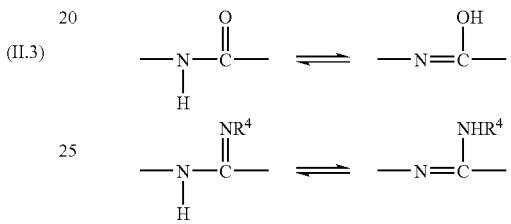

The ligands used in accordance with the invention preferably have at least one structural element of the general formulae I.a or I.b

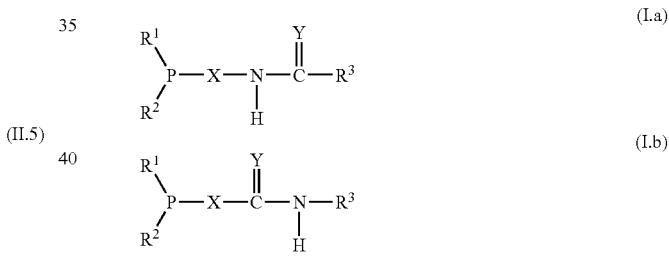

or tautomers thereof where
R$^1$ and R$^2$ are each independently alkyl, alkoxy, cycloalkyl, cycloalkoxy, heterocycloalkyl, heterocycloalkoxy, aryl, aryloxy, hetaryl or hetaryloxy,
R$^3$ is hydrogen or is as defined for R$^1$ and R$^2$,
X is a bivalent bridging group having from 1 to 5 bridging atoms between the flanking bonds,
Y is O, S or NR$^4$ where R$^4$ is hydrogen, alkyl, cycloalkyl, heterocycloalkyl, aryl or hetaryl,
and two or more than two of the X radicals and R$^1$ to R$^4$ together with the structural element of the formula I.a or I.b to which they are bonded may be a mono- or polycyclic compound.

With regard to suitable and preferred R$^1$ and R$^2$ radicals, reference is made to the preceding remarks.

The bivalent bridging X group preferably has from 1 to 4, more preferably from 1 to 3, bridging atoms between the flanking bonds.

The bivalent bridging X group is preferably a C$_1$–C$_5$-alkylene bridge which, depending on the number of bridging atoms, may have one or two double bonds and/or one, two, three or four substituents which are selected from alkyl, cycloalkyl, heterocycloalkyl, aryl, hetaryl, carboxylate, sulfonate, phosphonate, $NE^1E^2$ ($E^1$, $E^2$=hydrogen, alkyl, cycloalkyl, acyl or aryl), hydroxyl, thiol, halogen, nitro, acyl or cyano, and the cycloalkyl, aryl and hetaryl substituents may additionally bear one, two or three substituents which are selected from alkyl, alkoxy, halogen, trifluoromethyl, nitro, alkoxycarbonyl and cyano, and/or one or two nonadjacent bridging atoms of the $C_1$–$C_5$-alkylene bridge X may be replaced by a heteroatom or a heteroatom-containing group, and/or the alkylene bridge X may be singly or doubly fused with aryl and/or hetaryl, and the fused aryl and hetaryl groups may each bear one, two or three substituents which are selected from alkyl, cycloalkyl, aryl, alkoxy, cycloalkoxy, aryloxy, acyl, halogen, trifluoromethyl, nitro, cyano, carboxyl, alkoxycarbonyl or $NE^1E^2$ ($E^1$ and $E^2$=hydrogen, alkyl, cycloalkyl, acyl or aryl) and/or two or more than two bridging atoms of the $C_1$–$C_5$-alkylene bridge X together with the structural element of the formula I.a or I.b to which they are bonded may be a mono- or polycyclic compound.

X is preferably a $C_1$–$C_5$-alkylene bridge which may have one or two double bonds. In addition, two or more than two of the bridging atoms of the bridge X together with the structural element of the formula I.a or I.b to which they are bonded may preferably be a mono- or polycyclic compound.

The ligands used in accordance with the invention preferably have at least one structural element of the general formulae I.a or I.b in which the X group and the $R^3$ radical together with the —NH—C(=Y)— group to which they are bonded are a 5- to 8-membered, preferably 6-membered ring. This ring may have one, two or three double bonds, and one of these double bonds may be based on a tautomeric —N=C(YH)— group Preference is given to 6-membered rings which, taking into account the tautomerization, have three double bonds. Such ring systems in which one of the tautomers may form an aromatic ring system are particularly stable. The rings mentioned may be unsubstituted or have one, two, three, four or five of the aformentioned substituents. These are preferably selected from $C_1$–$C_4$-alkyl, more preferably methyl, ethyl, isopropyl or tert-butyl, $C_1$–$C_4$-alkoxy, especially methoxy, ethoxy, isopropyloxy or tert-butyloxy, and also aryl, preferably phenyl. In a suitable embodiment, the rings mentioned have at least one double bond, and the radicals bonded to this double bond are a fused ring system having 1, 2 or 3 further rings. These are preferably benzene or naphthalene rings. Fused benzene rings are preferably unsubstituted or have 1, 2 or 3 substituents which are selected from alkyl, alkoxy, carboxylate, sulfonate, halogen, $NE^1E^2$, trifluoromethyl, nitro, alkoxycarbonyl, acyl and cyano. Fused naphthalene rings are preferably unsubstituted or, in the nonfused and/or in the fused ring, each have 1, 2 or 3 of the substituents mentioned above for the fused benzene rings.

The ligands used in accordance with the invention are preferably selected from compounds of the general formulae I.1 to I.3

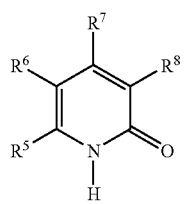
(I.1)

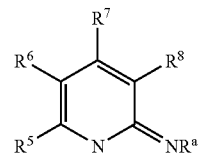
(I.2)

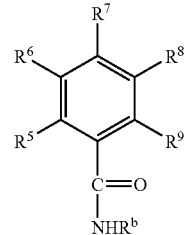
(I.3)

and the tautomers thereof where
one of the $R^5$ to $R^9$ radicals is a group of the formula —W'—PR$^1$R$^2$ where W' is a single bond, a heteroatom, a heteroatom-containing group or a bivalent bridging group having from 1 to 4 bridging atoms between the flanking bonds, $R^1$ and $R^2$ are each as defined above, the $R^5$ to $R^9$ radicals which are not W'—PR$^1$R$^2$ are each independently hydrogen, alkyl, cycloalkyl, heterocycloalkyl, aryl, hetaryl, WCOOR$^o$, WCOO$^-$M$^+$, W(SO$_3$)R$^o$, W(SO$_3$)$^-$M$^+$, WPO$_3$(R$^o$)(R$^p$), W(PO$_3$)$^{2-}$(M$^+$)$_2$, WNE$^1$E$^2$, W(NE$^1$E$^2$E$^3$)$^+$X$^-$, WOR$^q$, WSR$^q$, (CHR$^r$CH$_2$O)$_x$R$^q$, (CH$_2$NE$^1$)$_x$R$^q$, (CH$_2$CH$_2$NE$^1$)$_x$R$^q$, halogen, nitro, acyl or cyano, where W is a single bond, a heteroatom, a heteroatom-containing group or a bivalent bridging group having from 1 to 20 bridging atoms, R$^o$ and R$^p$ are each identical or different radicals selected from alkyl, cycloalkyl, acyl or aryl, R$^q$, E$^1$, E$^2$, E$^3$ are each identical or different radicals selected from hydrogen, alkyl, cycloalkyl, acyl and aryl, R$^r$ is hydrogen, methyl or ethyl, M$^+$ is one cation equivalent, X$^-$ is one anion equivalent and x is an integer from 1 to 240, and in each case two adjacent R$^5$, R$^6$, R$^7$, R$^8$ and R$^9$ radicals, together with the ring carbon atoms to which they are bonded, may also be a fused ring system having 1, 2 or 3 further rings, and R$^a$ and R$^b$ are each hydrogen, alkyl, acyl, cycloalkyl, heterocycloalkyl, aryl or hetaryl.

In a suitable embodiment of the process according to the invention, ligands of the general formulae I.1 to I.3 are used where $R^5$ and $R^6$ and/or $R^7$ and $R^8$ are each a fused ring system having 1, 2 or 3 further rings. When $R^5$ and $R^6$ and/or $R^7$ and $R^8$ are each a fused-on, i.e. fused, ring system, they are preferably benzene or naphthalene rings. Fused benzene rings are preferably unsubstituted and have 1, 2 or 3, in particular 1 or 2, substituents which are preferably selected from alkyl, alkoxy, halogen, SO$_3$H, sulfonate, NE$^1$E$^2$, alkylene-NE$^1$E$^2$, trifluoromethyl, nitro, COOR$^o$, alkoxycarbonyl, acyl and cyano. Fused naphthalene rings are preferably unsubstituted or have, in the nonfused ring and/or in the fused ring, in each case 1, 2 or 3, in particular 1 or 2, of the substituents specified above for the fused benzene rings. $R^7$ and $R^8$ are preferably each a fused-on ring system. In that case, $R^6$ and $R^9$ are preferably each hydrogen, or one of these radicals is hydrogen and the other a substituent which is selected from $C_1$- to $C_8$-alkyl, preferably $C_1$- to $C_4$-alkyl, especially methyl, ethyl, isopropyl or tert-butyl.

In the compounds of the formulae I.1 to I.3, the $R^5$ radical is preferably a group of the formula —W'—$PR^1R^2$ as defined above.

In the groups of the formula —W'—$PR^1R^2$, W' is preferably an oxygen atom or a single bond between the $PR^1R^2$ group and a ring carbon atom to which this group is bonded.

In the compounds of the formulae I.1 to I.3, the $R^1$ and $R^2$ radicals are preferably each independently $C_1$–$C_8$-alkyl such as methyl, ethyl, isopropyl and tert-butyl, $C_5$–$C_8$-cycloalkyl such as cyclohexyl, or aryl such as phenyl. The $R^1$ and $R^2$ radicals are preferably both aryl, in particular both phenyl.

In the compounds I.1 to I.3, the $R^6$, $R^7$, $R^8$ and $R^9$ radicals are preferably each independently selected from hydrogen, $C_1$–$C_4$-alkyl, $C_1$–$C_4$-alkoxy, carboxylate, sulfonate, $NE^1E^2$, halogen, trifluoromethyl, nitro, alkoxycarbonyl, acyl and cyano. $R^6$, $R^7$, $R^8$ and $R^9$ are preferably each hydrogen. Moreover, the $R^7$ and $R^8$ radicals, together with the ring carbon atoms to which they are bonded, are preferably a fused-on ring system as defined above, in particular a benzene ring. In that case, the $R^6$ and, where present, $R^9$ radicals are preferably each hydrogen.

In the compound of the formula I.2, the $R^a$ radical is preferably hydrogen, $C_1$–$C_8$-alkyl such as methyl, ethyl, isopropyl and tert-butyl, acyl, $C_5$–$C_8$-cycloalkyl such as cyclohexyl, or $C_6$–$C_{10}$-aryl such as phenyl. $R^a$ is more preferably acyl, in particular alkanoyl such as acetyl, propanoyl, butanoyl, isobutanoyl and pivaloyl.

In the compounds of the formula I.3, the $R^b$ radical is preferably hydrogen, $C_1$–$C_8$-alkyl such as methyl, ethyl, isopropyl and tert-butyl, $C_5$–$C_8$-cycloalkyl such as cyclohexyl, $C_6$–$C_{10}$-aryl such as phenyl, or hetaryl.

The compounds of the formulae I.1 to I.3 (as defined above and detailed more precisely hereinbelow), irrespective of their capability of forming intermolecular noncovalent bonds, are also suitable as ligands in hydroformylation catalysts. The invention therefore also provides a process for hydroformylating compounds which contain at least one ethylenically unsaturated double bond by reacting with carbon monoxide and hydrogen in the presence of a catalyst comprising at least one complex of a metal of transition group VIII of the Periodic Table of the Elements with ligands which are selected from compounds of the general formulae I.1 to I.3.

The ligands used in accordance with the invention are preferably selected from compounds of the general formulae I.i. to I.iii

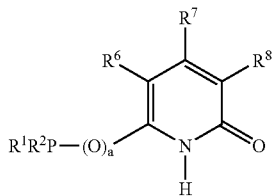
(I.i)

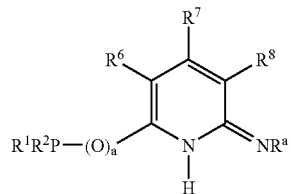
(I.ii)

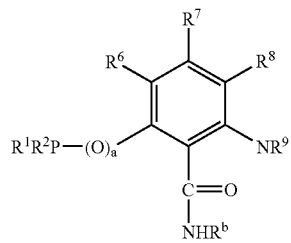
(I.iii)

and the tautomers thereof where
a is 0 or 1,
$R^1$ and $R^2$ are each as defined above,
$R^6$ to $R^9$ are each independently hydrogen, $C_1$–$C_4$-alkyl, $C_1$–$C_4$-alkoxy, acyl, aryl, heteroaryl, halogen, $C_1$–$C_4$-alkoxycarbonyl or carboxylate,
and in each case two adjacent $R^6$, $R^7$, $R^8$ and $R^9$ radicals, together with the ring carbon atoms to which they are bonded, may also be a fused ring system having 1, 2 or 3 further rings, and
$R^a$ and $R^b$ are each hydrogen, alkyl, acyl, cycloalkyl or aryl.

In the compounds of the formulae I.i to I.iii, the $R^1$ and $R^2$ radicals are preferably each independently $C_1$–$C_8$-alkyl such as methyl, ethyl, isopropyl and tert-butyl, $C_5$–$C_8$-cycloalkyl such as cyclohexyl, or aryl such as phenyl. The $R^1$ and $R^2$ radicals are preferably both aryl, in particular both phenyl.

The $R^6$, $R^7$, $R^8$ and $R^9$ radicals in the compounds I.i to I.iii are preferably each independently selected from hydrogen, $C_1$–$C_4$-alkyl, $C_1$–$C_4$-alkoxy, carboxylate, sulfonate, $NE^1E^2$, halogen, trifluoromethyl, nitro, alkoxycarbonyl, acyl and cyano. $R^6$, $R^7$, $R^8$ and $R^9$ are preferably each hydrogen. Moreover, the $R^7$ and $R^8$ radicals, together with the ring carbon atoms to which they are bonded, are preferably a fused-on ring system as defined above, in particular a benzene ring. In that case, $R^6$ and, where present, $R^9$ are preferably each hydrogen.

In the compounds of the formula I.ii, the $R^a$ radical is preferably hydrogen, $C_1$–$C_8$-alkyl such as methyl, ethyl, isopropyl and tert-butyl, $C_5$–$C_8$-cycloalkyl such as cyclohexyl, or $C_6$–$C_{10}$-aryl such as phenyl. $R^a$ is more preferably acyl, in particular alkanoyl such as acetyl, propanoyl, butanoyl, isobutanoyl and pivaloyl.

In the compounds of the formula I.iii, the $R^b$ radical is preferably hydrogen, $C_1$–$C_8$-alkyl such as methyl, ethyl, isopropyl and tert-butyl, $C_5$–$C_8$-cycloalkyl such as cyclohexyl, or $C_6$–$C_{10}$-aryl such as phenyl or hetaryl.

Some advantageous compounds are listed hereinbelow, also including their tautomers:

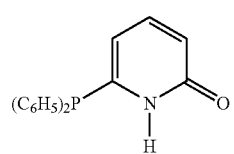
(1)

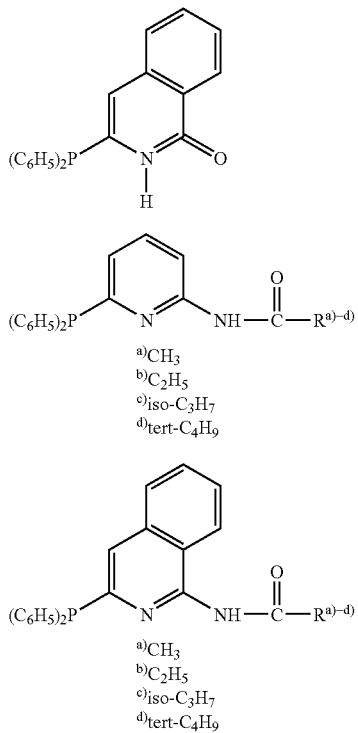

An example of a ligand which can be used particularly advantageously in accordance with the invention is 6-diphenylphosphino-1-H-pyridin-2-one.

The aforementioned ligands of the formulae I.1 to I.3, especially of the formulae I.i to I.iii and more especially of the formulae (1) to (4) are suitable either as sole ligands, in which case homo-dimer formation is assumed, or in ligand combinations, in which case at least partial hetero-dimer formation is assumed. In the case of ligand combinations, all ligands may be selected from ligands of the formulae I.1 to I.3 and especially from ligands of the formulae I.i to I.iii, more especially (1) to (4). However, it is also possible to select only at least one of the ligands of a ligand combination from ligands of the formulae specified and combine it with at least one different ligand. Suitable for combination (as one component of a hetero-dimer) are preferably ligands which are selected from compounds of the following formula II (II)

$$\begin{array}{c} R^{12} \\ R^{11} \diagup \diagdown R^{13} \\ R^{10} \diagdown N \diagup R^{14} \end{array}$$

where
one of the $R^{10}$ to $R^{14}$ radicals is a group of the formula —W"—$PR^1R^2$, where
W" is a single bond, a hetero atom, a hetero atom-containing group or a divalent bridging group having from 1 to 4 bridging atoms between the flanking bonds, $R^1$ and $R^2$ are each independently alkyl, alkoxy, cycloalkyl, cycloalkoxy, heterocycloalkyl, heterocycloalkoxy, aryl, aryloxy, hetaryl or hetaryloxy,
the $R^{10}$ to $R^{14}$ radicals which are not —W"—$PR^1R^2$ are each independently hydrogen, alkyl, cycloalkyl, heterocycloalkyl, aryl, hetaryl, $WCOOR^s$, $WCOO^-M^+$, $W(SO_3)R^s$, $W(SO_3)^-M^+$, $WPO_3(R^s)(R^t)$, $W(PO_3)^{2-}(M^+)_2$, $WNE^7E^8$, $W(NE^7E^8E^9)^+X^-$, $WOR^u$, $WSR^u$, $(CHR^vCH_2O)_zR^u$, $(CH_2NE^7)_zR^u$, $(CH_2CH_2NE^7)_zR^u$, halogen, nitro, acyl or cyano,
where
W is a single bond, a hetero atom, a hetero atom-containing group or a divalent bridging group having from 1 to 20 bridging atoms,
$R^s$ and $R^t$ are each identical or different radicals selected from alkyl, cycloalkyl, acyl and aryl,
$R^u$, $E^7$, $E^8$, $E^9$ are each identical or different radicals selected from hydrogen, alkyl, cycloalkyl, acyl and aryl,
$R^v$ is hydrogen, methyl or ethyl,
$M^+$ is one cation equivalent,
$X^-$ is one anion equivalent and
z is an integer from 1 to 240,
and in each case two adjacent $R^{10}$, $R^{11}$, $R^{12}$, $R^{13}$ and $R^{14}$ radicals, together with the ring carbon atoms to which they are bonded, may also be a fused ring system having 1, 2 or 3 further rings.

In the compounds of the formula II, the $R^{10}$ radical is preferably a group of the formula —W"—$PR^1R^2$ as defined above.

In the groups of the formula —W"—$PR^1R^2$, W" is preferably an oxygen atom or a single bond between the $PR^1R^2$ group and a ring carbon atom to which this group is bonded.

In the compounds of the formula II, the $R^1$ and $R^2$ radicals are preferably each independently $C_1$–$C_8$-alkyl such as methyl, ethyl, isopropyl and tert-butyl, $C_5$–$C_8$-cycloalkyl such as cyclohexyl, or aryl such as phenyl. The $R^1$ and $R^2$ radicals are preferably both aryl, in particular both phenyl.

In the compounds of the formula II, the $R^{11}$, $R^{12}$, $R^{13}$ and $R^{14}$ radicals are preferably each independently selected from hydrogen, $C_1$–$C_4$-alkyl, $C_1$–$C_4$-alkoxy, carboxylate, sulfonate, $NE^1E^2$, halogen, trifluoromethyl, nitro, alkoxycarbonyl, acyl and cyano. $R^6$, $R^7$, $R^8$ and $R^9$ are preferably each hydrogen. Moreover, the $R^{12}$ and $R^{13}$ radicals, together with the ring carbon atoms to which they are bonded, are preferably a fused-on ring system as defined above, in particular a benzene ring. In that case, the $R^{11}$ and $R^{14}$ radicals are preferably each hydrogen.

A preferred compound of the formula II is 2-(diphenylphosphino)pyridine.

For illustration, some preferred ligand/ligand pairs are listed hereinbelow:

| Ligand 1 | Ligand 2 |
|---|---|
| (5) 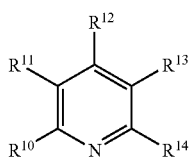 | |

-continued

| Ligand 1 | Ligand 2 |
|---|---|
| (6) [3-PPh2-isoquinolin-1(2H)-one] | [N-(6-PPh2-pyridin-2-yl) pivalamide] |
| (7) [3-PPh2-isoquinolin-1(2H)-one] | [N-(6-PPh2-pyridin-2-yl)acetamide] |
| (8) [3-PPh2-isoquinolin-1(2H)-one] | [2-PPh2-pyridine] |

The ligands which can be used in accordance with the invention can be prepared by customary processes known to those skilled in the art.

In J. Org. Chem. 2000, 65, p. 6917–6921, M. Akazome et al. describe the synthesis of (2-oxo-1,2-dihydro-x-pyridyl) diphenylphosphines where x=3, 5 and 6 (3-, 5- and 6-diphenylphosphino-2-pyridinones) by lithiating the corresponding 2-benzoyloxy-x-bromopyridines, subsequently coupling with chlorodiphenylphosphine and finally detaching the benzoyl protecting group with trifluoroacetic acid. With regard to the preparation of the 2-benzoyloxy-x-bromopyridines used as reactants, reference is made to the process described by Y. Dycharme and J. D. Wüst in J. Org. Chem. 1988, 53, p. 5787.

In J. Org. Chem. 1978, 43, p. 947–949, G. R. Newkome and D. C. Hager describe a process for preparing pyridyldiphenylphosphines by reacting lithium diphenylphosphite with halopyridines. Afterward, 6-diphenylphosphinopyridinone is obtained from lithium diphenylphosphide and 6-chloro-2-methoxypyridine.

The aforementioned documents are fully incorporated by way of reference.

A novel process for preparing phosphinopyridinones and/or tautomers thereof comprises the reaction of a pyridine compound which bears a protected hydroxyl group and a nucleophilically displaceable group with a solution of a phosphine and of an alkali metal in liquid ammonia to obtain at least one pyridine compound which bears a protected hydroxyl group and a phosphino group, and the subsequent detachment of the protecting group of the hydroxyl group. This process does not form part of the subject matter of the present application, but rather of the parallel German patent application 103 13 320.8, which is incorporated herein by way of reference.

The present invention further provides a catalyst comprising at least one complex of a metal of transition group VIII of the Periodic Table of the Elements with ligands which each have a phosphorus group and at least one functional group capable of forming intermolecular noncovalent bonds, the complex having ligands dimerized via intermolecular noncovalent bonds and the distance between the phosphorus atoms of the dimerized ligands being at most 5 Å. Reference is made to all of the preceding remarks on suitable and preferred ligands.

The invention further provides a catalyst comprising at least one complex of a metal of transition group VIII of the Periodic Table having at least one ligand which is selected from the compounds of the general formulae I.1 to I.3 as defined above. Reference is made to all of the preceding remarks on suitable and preferred ligands I.1 to 1.3.

The inventive catalysts which are used in accordance with the invention preferably have two or more than two of the above-described compounds as ligands. At least two of the ligands are preferably present in dimerized form. In addition to the above-described ligands, they may also have at least one further ligand which is preferably selected from halides, amines, carboxylates, acetylacetonate, aryl- and alkylsulfonates, hydride, CO, olefins, dienes, cycloolefins, nitriles, N-containing heterocycles, aromatics and heteroaromatics, ethers, $PF_3$, phospholes, phosphabenzenes and also mono-, di- and multidentate phosphine, phosphinite, phosphonite, phosphoramidite and phosphite ligands.

The metal of transition group VIII is preferably cobalt, ruthenium, rhodium, palladium, platinum, osmium or iridium, and in particular cobalt, rhodium, ruthenium and iridium.

In general, the particular catalysts or catalyst precursors used, under hydroformylation conditions, form catalytically active species of the general formula $H_xM_y(CO)_zL_q$ where M is a metal of transition group VIII, L is a phosphorus compound of the formula I and q, x, y, z are integers dependent upon the valency and type of the metal and also on the valency of the L ligand. z and q are preferably each independently a value of at least 1, for example 1, 2 or 3. The sum of z and q is preferably a value from 1 to 5. The complexes may, if desired, additionally have at least one of the above-described further ligands. There is reason to assume that the catalytically active species also has dimerized ligands (pseudochelates).

In a preferred embodiment, the hydroformylation catalysts are prepared in situ, in the reactor used for the hydroformylation reaction. However, the catalysts according to the invention may, if desired, also be prepared separately and be isolated by customary processes. To prepare the catalysts according to the invention in situ, for example, at least one ligand used in accordance with the invention, a compound or a complex of a metal of transition group VIII, optionally at least one further additional ligand and optionally an activator may be reacted in an inert solvent under the hydroformylation conditions.

Suitable rhodium compounds or complexes are, for example, rhodium(II) and rhodium(III) salts such as rhodium(III) chloride, rhodium(III) nitrate, rhodium(II) sulfate, potassium rhodium sulfate, rhodium(II) or rhodium(III) carboxylate, rhodium(II) and rhodium(III) acetate, rhodium(III) oxide, salts of rhodium(III) acid, trisammonium-hexachlororhodate(III), etc. Also suitable are rhodium complexes such as rhodium biscarbonyl acetylacetonate, acetylacetonatobisethylenerhodium(I), etc. Preference is given to using rhodium biscarbonyl acetylacetonate or rhodium acetate.

Likewise suitable are ruthenium salts or compounds. Suitable ruthenium salts are, for example, ruthenium(III) chloride, ruthenium(IV), ruthenium(VI) or ruthenium(VIII) oxide, alkali metal salts of ruthenium-oxygen acids such as K₂RuO₄ or KRuO₄, or complexes, for example RuHCl(CO)(PPh₃)₃. Also useful in the process according to the invention are the metal carbonyls of ruthenium such as trisruthenium dodecacarbonyl or hexaruthenium octadecacarbonyl, or mixed forms in which CO has been partly replaced by ligands of the formula PR₃ such as Ru(CO)₃(PPh₃)₂.

Suitable cobalt compounds are, for example, cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthanoate, and also the cobalt caproate complex. The carbonyl complexes of cobalt such as dicobalt octacarbonyl, tetracobalt dodecacarbonyl and hexacobalt hexadecacarbonyl may also be used here.

The compounds of cobalt, rhodium, ruthenium and iridium which have been mentioned and are further suitable compounds are known in principle and adequately described in the literature, or may be prepared by those skilled in the art in a similar manner to the compounds already known.

Suitable activators are, for example, Brönsted acids, Lewis acids, for example BF₃, AlCl₃, ZnCl₂, and Lewis bases.

The solvents are preferably the aldehydes which are formed in the hydroformylation of the particular olefins, and also their higher-boiling subsequent reaction products, for example the products of the aldol condensation. Solvents which are likewise suitable are aromatics such as toluene and xylenes, hydrocarbons or mixtures of hydrocarbons, also for diluting the abovementioned aldehydes and the subsequent products of the aldehydes. Further solvents are esters of aliphatic carboxylic acids with alkanols, for example ethyl acetate or Texanol™, ethers such as tert-butyl methyl ether and tetrahydrofuran.

It is also possible to carry out the reactions in water or aqueous solvent systems which, in addition to water, contain a water-miscible solvent, for example a ketone such as acetone and methyl ethyl ketone or another solvent. For this purpose, ligands are used which have been modified with polar groups, for example ionic groups such as $SO_3^-M^+$, $CO_2^-M^+$ where $M^+=Na^+$, $K^+$ or $NH_4^+$, or such as $N(CH_3)_4^+$. The reactions are then effected in a biphasic catalysis, in which the catalyst is in the aqueous phase and feedstocks and products form the organic phase. The reaction may also be configured as a biphasic catalysis in ionic liquids.

The molar ratio of monophosphorus ligands to metal of transition group VIII is generally in the range from about 1:1 to 1000:1, preferably from 2:1 to 500:1.

Useful substrates for the hydroformylation process according to the invention are in principle all compounds which contain one or more ethylenically unsaturated double bonds. These include, for example, olefins such as α-olefins, internal straight-chain and internal branched olefins. Preference is given to using α-olefins, for example ethylene, propene, 1-butene, 1-pentene, 1-hexene, 1-heptene, 1-octene, 1-nonene, 1-decene, 1-undecene, 1-dodecene, etc.

Suitable branched, internal olefins are preferably $C_4$–$C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc.

Suitable olefins to be hydroformylated are also $C_5$–$C_8$-cycloalkenes such as cyclopentene, cyclohexene, cycloheptene, cyclooctene and derivatives thereof, for example their $C_1$–$C_{20}$-alkyl derivatives having from 1 to 5 alkyl substituents. Suitable olefins to be hydroformylated are also vinylaromatics such as styrene, α-methylstyrene, 4-isobutylstyrene, etc. Suitable olefins to be hydroformylated are also α,β-ethylenically unsaturated mono- and/or dicarboxylic acids, their esters, monoesters and amides, such as acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., $C_1$–$C_{20}$-alkenols, -alkenediols and -alkadienols such as 2,7-octadienol-1. Suitable substrates are also di- or polyenes having isolated or conjugated double bonds. These include, for example, 1,3-butadiene, 1,4-pentadiene, 1,5-hexadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, vinylcyclohexene, dicyclopentadiene, 1,5,9-cyclooctatriene and also butadiene homo- and copolymers.

In a suitable embodiment, the unsaturated compound used for hydroformylation is selected from internal linear olefins and olefin mixtures which contain at least one internal linear olefin. Suitable linear (straight-chain) internal olefins are preferably $C_4$–$C_{20}$-olefins such as 2-butene, 2-pentene, 2-hexene, 3-hexene, 2-heptene, 3-heptene, 2-octene, 3-octene, 4-octene, etc., and mixtures thereof.

The inventive catalysts which are used in accordance with the invention are also advantageously suitable for hydroformylating functionalized olefins, in particular functionalized 1-olefins. The olefins to be hydroformylated are preferably selected from compounds of the general formula III

$$CH_2=CH-Z-(Fu)_n \quad (III)$$

where

Z is a bivalent bridging group having from 1 to 20 bridging atoms between the flanking bonds and Fu is a functional group, and n is an integer from 1 to 4.

The bivalent bridging group Z is preferably a $C_1$–$C_{20}$-alkylene bridge which, depending on the number of bridging atoms, may have one, two, three or four double bonds and/or one, two, three or four substituents, and the cycloalkyl, aryl and heteroaryl substituents may in turn additionally bear one, two or three substituents which are selected from alkyl, alkoxy, halogen, trifluoromethyl, nitro, alkoxycarbonyl and cyano, and/or from 1 to 10 nonadjacent bridging atoms of the $C_1$–$C_{20}$-alkylene bridge Z may be replaced by a heteroatom or a heteroatom-containing group, and/or the alkylene bridge Z may be singly or doubly fused with aryl and/or hetaryl, in which case the fused aryl and hetaryl groups may bear one, two or three substituents which are selected from alkyl, cycloalkyl, aryl, alkoxy, cycloalkoxy, aryloxy, acyl, halogen, trifluoromethyl, nitro, cyano, carboxyl, alkoxycarbonyl or $NE^1E^2$ ($E^1$ and $E^2$=hydrogen, alkyl, cycloalkyl, acyl or aryl).

The functional group Fu is preferably selected from —OH, —SH, —Cl, —Br, —COOR¹⁵, —O—C(=O)R¹⁶, —O—C(=O)—OR¹⁵, —O—C(=)—NR¹⁶R¹⁷, —NR¹⁷—C(=O)—R¹⁶, —NR¹⁷—C(=O)—OR¹⁵, —NR¹⁶—C(=O)—NR¹⁷R¹⁸, where $R^{15}$ is alkyl, cycloalkyl, heterocycloalkyl, aryl or hetaryl $R^{16}$, $R^{17}$ and $R^{18}$ are each independently hydrogen, alkyl, cycloalkyl, heterocycloalkyl, aryl or hetaryl.

Merely for illustration, some suitable functionalized olefins are listed hereinbelow:

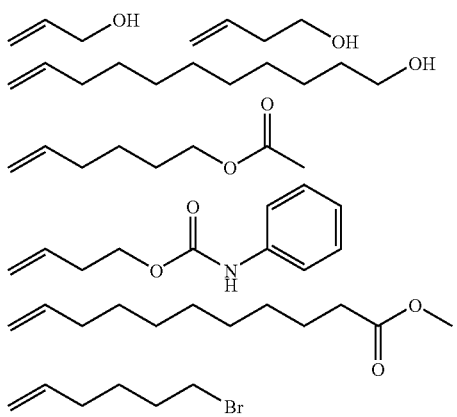

In the hydroformylation process according to the invention, preference is given to using an olefin mixture which is obtainable on the industrial scale and in particular contains at least one internal olefin. These include, for example, the Ziegler olefins obtained by selective ethene oligomerization in the presence of alkylaluminum catalysts. These are substantially unbranched olefins having a terminal double bond and an even number of carbon atoms. These also include olefins obtained by ethene oligomerization in the presence of different catalyst systems, for example the predominantly linear α-olefins obtained in the presence of alkylaluminum chloride/titanium tetrachloride catalysts and the α-olefins obtained in the presence of nickel-phosphine complex catalysts by the Shell Higher Olefin Process (SHOP). Suitable industrially available olefin mixtures are also obtained in the paraffin dehydrogenation of appropriate crude oil fractions, for example what are known as petroleum or diesel oil fractions. For the conversion of paraffins, predominantly of n-paraffins to olefins, essentially three processes are used:

thermal cracking (steam cracking), catalytically dehydrogenating and chemically dehydrogenating by chlorinating and dehydrochlorinating.

Thermal cracking leads predominantly to α-olefins, while the other variants result in olefin mixtures which generally also have relatively large proportions of olefins having internal double bonds. Suitable olefin mixtures are also the olefins obtained in the metathesis and telomerization reactions. These include, for example, the olefins from the Phillips triolefin process, a modified SHOP process composed of ethylene oligomerization, double bond isomerization and subsequent metathesis (ethenolysis).

Suitable technical olefin mixtures which can be used in the hydroformylation process according to the invention are also selected from dibutenes, tributenes, tetrabutenes, dipropenes, tripropenes, tetrapropenes, mixtures of butene isomers, in particular raffinate II, dimeric butenes, dihexenes, dimers and oligomers from the Dimersol® process from IFP, Octol process® from Hüls, Polygas process, etc.

Preference is given to a process, wherein the hydroformylation catalyst is prepared in situ by reacting at least one ligand which can be used in accordance with the invention, a compound or a complex of a metal of transition group VIII and optionally an activator in an inert solvent under the hydroformylation conditions.

The hydroformylation reaction may be effected continuously, semicontinuously or batchwise.

Suitable reactors for the continuous reaction are known to those skilled in the art and are described, for example, in Ullmanns Enzyklopädie der technischen Chemie, vol. 1, 3rd ed., 1951, p. 743 ff.

Suitable pressure-rated reactors are likewise known to those skilled in the art and are described, for example in Ullmanns Enzyklopädie der technischen Chemie, vol. 1, 3rd ed., 1951, p. 769 ff. In general, an autoclave is used for the process according to the invention and may, if desired, be provided with a stirrer apparatus and an internal lining.

The composition of the synthesis gas which is used in the process according to the invention and is composed of carbon monoxide and hydrogen may vary within wide ranges. The molar ratio of carbon monoxide to hydrogen is generally from about 5:95 to 70:30, preferably from about 40:60 to 60:40. Particular preference is given to using a molar ratio of carbon monoxide to hydrogen in the range of about 1:1.

The temperature in the hydroformylation reaction is generally in the range of from about 20 to 180° C., preferably from about 50 to 150° C. In general, the pressure is in the range from about 1 to 700 bar, preferably from 1 to 600 bar, in particular from 1 to 300 bar. Depending on the activity of the hydroformylation catalyst according to the invention used, the reaction pressure may be varied. In general, the catalysts according to the invention based on phosphorus compounds permit reaction in the range of low pressures, for instance in the range from 1 to 100 bar.

The inventive hydroformylation catalysts used in accordance with the invention can be removed from via effluent of the hydroformylation reaction by processes known to those skilled in the art and may generally be reused for the hydroformylation.

The above-described catalysts may also be immobilized in a suitable manner, for example by binding via functional groups suitable as anchor groups, adsorption, grafting, etc., on a suitable support, for example on glass, silica gel, synthetic resins, polymers, etc. They are then also suitable for use as solid phase catalysts.

The hydroformylation activity of catalysts based on the above-described ligands is surprisingly generally higher than the isomerization activity with respect to the formation of internal double bonds. Advantageously, the inventive catalysts used in accordance with the invention have a high selectivity in favor of the α-aldehydes or -alcohols in the hydroformylation of α-olefins. In addition, the catalysts according to the invention are also suitable for hydroformylating a multitude of substituted olefins which are otherwise not readily amenable to hydroformylation. In addition, the catalysts generally have high stability under the hydroformylation conditions, so that they can generally be used to achieve longer catalyst on-stream times than the prior art catalysts based on conventional chelate ligands. Advantageously, the inventive catalysts used in accordance with the invention also have high activity, so that the corresponding aldehydes or alcohols can generally be obtained in good yields. In the hydroformylation of α-olefins and also of internal, linear olefins, they additionally exhibit very low selectivity for the hydrogenation product of the olefin used.

The invention further provides a process for preparing 2-propylheptanol, by
a) hydroformylating butene or a butene-containing $C_4$-hydrocarbon mixture in the presence of a catalyst as defined above with carbon monoxide and hydrogen to obtain an n-valeraldehyde-containing hydroformylation product,
b) optionally subjecting the hydroformylation product to a separation to obtain an n-valeraldehyde-enriched fraction, c) subjecting the hydroformylation product obtained in step a) or the n-valeraldehyde-enriched fraction obtained in step b) to an aldol condensation, d) catalytically hydrogenating the products of the aldol condensation with hydrogen to give alcohols, and e) optionally subjecting the hydrogenation products to a separation to obtain a 2-propylheptanol-enriched fraction.

a) Hydroformylation

Suitable starting materials for the hydroformylation are both substantially pure 1-butene and mixtures of 1-butene with 2-butene and industrially available $C_4$ hydrocarbon streams which comprise 1-butene and/or 2-butene. Preference is given to $C_4$ cuts which are available in large amounts from FCC plants and steam crackers. These consist substantially of a mixture of the isomeric butenes and butane.

$C_4$ hydrocarbon streams suitable as a starting material contain, for example, from 50 to 99 mol %, preferably from 60 to 90 mol %, of butenes, and from 1 to 50 mol %, preferably from 10 to 40 mol %, of butanes. The butene fraction preferably includes from 40 to 60 mol % of 1-butene, from 20 to 30 mol % of 2-butene and less than 5 mol %, in particular less than 3 mol %, of isobutene (based on the butene fraction). A particularly preferred feedstock which is used is what is known as raffinate II, which is an isobutene-depleted $C_4$ cut from an FCC plant or a steam cracker.

Hydroformylation catalysts based on the phosphorus chelate compounds used in accordance with the invention as ligands advantageously have high n-selectivity, even when 2-butene and 2-butenic hydrocarbon mixtures are used as the starting material. This also allows such feedstocks to be used economically in the process according to the invention, since the desired n-valeraldehyde results in good yields.

b) Separation

In a suitable process variant, the product-enriched fraction obtained in step a) after the catalyst system has been removed is subjected to a further separation to obtain an n-valeraldehyde-enriched fraction. The hydroformylation product is separated into an n-valeraldehyde-enriched fraction and an n-valeraldehyde-depleted fraction by customary processes known to those skilled in the art. Preference is given to distillation using known separating apparatus such as distillation columns, for example tray columns, which may, if desired, be equipped with bubble-caps, sieve plates, sieve trays, valves, etc., evaporators such as thin-film evaporators, falling-film evaporators, wiped-blade evaporators, etc.

c) Aldol condensation

Two molecules of $C_5$-aldehyde may be condensed to give α,β-unsaturated $C_{10}$-aldehydes. The aldol condensation is effected in a manner known per se, for example by the action of an aqueous base such as sodium hydroxide solution or potassium hydroxide solution. Alternatively, a heterogeneous basic catalyst such as magnesium oxide and/or aluminum oxide may be used (cf., for example, EP-A 792 862). The condensation of two molecules of n-valeraldehyde results in 2-propyl-2-heptenal. When the hydroformylation product obtained in step a) or after the separation in step b) also comprises further $C_5$-aldehydes such as 2-methylbutanal and in some cases 2,2-dimethylpropanal, these likewise undergo an aldol condensation, resulting in the condensation products of all possible aldehyde combinations, for example 2-propyl-4-methyl-2-hexenal. A proportion of these condensation products, for example of up to 30% by weight, does not prevent advantageous further processing to 2-propylheptanol-containing $C_{10}$-alcohol mixtures which are suitable as plasticizer alcohols.

d) Hydrogenation

The products of the aldol condensation may be catalytically hydrogenated with hydrogen to $C_{10}$-alcohols, in particular 2-propylheptanol.

For the hydrogenation of the $C_{10}$-aldehydes to the $C_{10}$-alcohols, the catalysts of the hydroformylation are in principle usually also suitable at relatively high temperatures; however, preference is generally given to more selective hydrogenation catalysts which are used in a separate hydrogenation stage. Suitable hydrogenation catalysts are generally transition metals, for example, Cr, Mo, W, Fe, Rh, Co, Ni, Pd, Pt, Ru etc., or mixtures thereof, which may be applied to supports, for example activated carbon, aluminum oxide, kieselguhr, etc., to increase the activity and stability. To increase the catalytic activity, Fe, Co and preferably Ni, also in the form of the Raney catalysts, may be used as metal sponge having a very large surface area. Depending on the activity of the catalyst, the $C_{10}$-aldehydes are hydrogenated preferably at elevated temperatures and elevated pressure. The hydrogenation temperature is preferably from about 80 to 250° C.; the pressure is preferably from about 50 to 350 bar.

The crude hydrogenation product may be worked up to give the $C_{10}$-alcohols by customary processes, for example by distillation.

e) Separation

If desired, the hydrogenation products may be subjected to a further separation to obtain a 2-propylheptanol-enriched fraction and a 2-propylheptanol-depleted fraction. This separation may be effected by customary processes known to those skilled in the art, for example by distillation.

Hydroformylation catalysts which comprise a complex of at least one metal of transition group VIII of the Periodic Table with a ligand which can be used in accordance with the invention are advantageously suitable for use in a process for preparing 2-propylheptanol. The catalysts have high n-selectivity, so that a good yield of n-valeraldehyde is obtained when either substantially pure 1-butene is used or when 1-butenic/2-butenic hydrocarbon mixtures are used, for example $C_4$ cuts.

The invention further provides the use of catalysts comprising at least one complex of a metal of transition group VIII with at least one ligand as described above for hydroformylating, carbonylating and for hydrogenating.

The invention is illustrated in detail with the aid of the nonlimiting examples which follow.

EXAMPLE A

Calculation of 6-diphenylphosphinopyridinone Dimers (6-DPPon Dimers) to Forecast Their Pseudochelate Properties With the aid of a graphic molecular modeling program, all possible hydrogen-bonded dimers of 6-DPPon and its tautomers are generated. These dimer structures are then optimized by quantum chemistry methods.

6-DPPon ligands are only suitable as chelate ligands when the separation of the phosphorus atoms in the calculated dimer structure is less than 5 Å.

The calculated dimer formation of 6-diphenylphosphinopyridone is shown hereinbelow. The calculation shows that the interaction of a 6-diphenylphosphinopyrid-2-one with 2-hydroxy-6-diphenylphosphinopyridine (a tautomer of 6-diphenylphosphinopyrid-2-one) leads to an arrangement in which the phosphorus atoms have a separation of 3.8 Å (Method: DFT, B3-LYP, basis: TZVP (A. Schäfer et al., J. Chem. Phys. (1994), 100, p. 5829 ff)). The system is thus capable of chelating and of its known associated advantages.

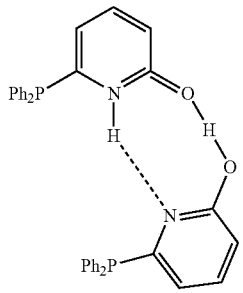

EXAMPLE B

Crystal Structure Analysis of [cis-PtCl$_2$(6-DPPon)$_2$]

In a Schlenk tube, 68.4 mg (182 μmol, 1 eq) of [cis-PtCl$_2$(COD)$_2$] were dissolved in 2.5 ml of CH$_2$Cl$_2$ and admixed with 102 mg (366 μmol, 2 eq) of 6-diphenylphosphino-1H-pyridin-2-one. The lemon-yellow suspension was admixed with a further 2.5 ml of CH$_2$Cl$_2$ and the resulting pale yellow solution stirred at room temperature for 5 min. After the solvent had been removed under high vacuum (HV), the remaining residue was suspended twice in 5 ml each time of pentane, the supernatant solvent was pipetted off and the white solid was dried under HV. Suitable crystals for a crystal structure analysis were obtained from a solution of 20 mg of [cis-PtCl$_2$(6-DPPon)$_2$] in 1 ml of CH$_2$Cl$_2$. FIG. 1 shows a ball-and-stick diagram of the structure determined.

TABLE 1

Data of the X-ray structural analysis

| | |
|---|---|
| Empirical formula | C$_{35}$ H$_{30}$ Cl$_4$ N$_2$ O$_2$ P$_2$ Pt |
| Molar mass | 909.44 |
| Temperature | 100(2) K |
| Wavelength | 0.71073 A |
| Crystal system, space group | Monoclinic, P 21/a |
| Lattice constants | a = 16.8292(3) Å alpha = 90° |
| | b = 11.1616(2) Å beta = 101.7809(11)° |
| | c = 18.6043(3) Å gamma = 90° |
| Volume | 3421.03(10) Å$^3$ |
| Z, density (calculated) | 4, 1.766 Mg/m^3 |
| Absorption coefficient | 4.543 mm$^{-1}$ |
| F(000) | 1784 |
| Crystal size | 0.43 × 0.3 × 0.25 mm |
| Theta range measured | 2.89 to 27.50° |
| Index limits | −21<=h<=21, −14<=k<=14, −14<=l<=24 |
| Measured/independent reflections | 19764/7783 [R(int) = 0.0313] |
| Absorption correction | semiempirical |
| Max. and min. transmission | 0.294 and 0.249 |
| Structure refining | least squares against F$^2$ |
| Data/restraints/parameters | 7783/0/423 |
| Goodness-of-fit on F^2 | 1.059 |
| R values [I>2σ(I)] | R1 = 0.0205, wR2 = 0.0478 |
| R values (all data) | R1 = 0.0250, wR2 = 0.0496 |
| Max/min residual electron density | 0.926 and −1.475 e Å$^3$ |

TABLE 2

Atom coordination and thermal parameters

| | x | Y | z | U(eq) |
|---|---|---|---|---|
| C(11) | 4628(1) | 111(2) | 8359(1) | 18(1) |
| C(12) | 4100(2) | 888(3) | 8588(2) | 26(1) |
| C(13) | 3794(2) | 560(3) | 9208(2) | 33(1) |
| C(14) | 4037(2) | −494(3) | 9555(2) | 32(1) |
| C(15) | 4595(2) | −1211(3) | 9295(2) | 26(1) |
| C(21) | 4594(1) | 1660(2) | 7075(1) | 16(1) |
| C(22) | 4806(2) | 2766(2) | 7407(2) | 22(1) |
| C(23) | 4465(2) | 3813(2) | 7085(2) | 26(1) |
| C(24) | 3904(2) | 3760(2) | 6423(2) | 24(1) |
| C(25) | 3693(2) | 2670(2) | 6086(1) | 25(1) |
| C(26) | 4034(2) | 1620(2) | 6407(1) | 21(1) |
| C(31) | 6094(1) | 725(2) | 7866(1) | 15(1) |
| C(32) | 6480(1) | 508(2) | 8588(1) | 19(1) |
| C(33) | 7287(2) | 843(2) | 8839(2) | 24(1) |
| C(34) | 7715(2) | 1378(2) | 8362(2) | 26(1) |
| C(35) | 7335(2) | 1603(2) | 7640(2) | 24(1) |
| C(36) | 6522(2) | 1294(2) | 7392(1) | 18(1) |
| C(41) | 6646(1) | −1924(2) | 7649(1) | 15(1) |
| C(42) | 7460(2) | −1791(2) | 7753(1) | 20(1) |
| C(43) | 7936(2) | −1990(3) | 8466(2) | 25(1) |
| C(44) | 7582(2) | −2311(2) | 9033(2) | 26(1) |
| C(45) | 6727(2) | −2440(2) | 8939(1) | 22(1) |
| C(51) | 6061(1) | −3465(2) | 6465(1) | 16(1) |
| C(52) | 5880(2) | −3750(2) | 5718(1) | 21(1) |
| C(53) | 5961(2) | −4912(3) | 5485(2) | 25(1) |
| C(54) | 6225(2) | −5805(3) | 5993(2) | 29(1) |
| C(55) | 6406(2) | −5537(2) | 6738(2) | 28(1) |
| C(56) | 6323(2) | −4371(2) | 6975(1) | 21(1) |
| C(61) | 6332(1) | −1021(2) | 6108(1) | 15(1) |
| C(62) | 7058(1) | −1329(2) | 5893(1) | 17(1) |
| C(63) | 7324(2) | −632(2) | 5367(1) | 21(1) |
| C(64) | 6881(2) | 347(3) | 5053(1) | 23(1) |
| C(65) | 6156(2) | 641(2) | 5256(1) | 22(1) |
| C(66) | 5878(2) | −51(2) | 5776(1) | 18(1) |
| Cl(1) | 3356(1) | −935(1) | 6987(1) | 18(1) |
| Cl(2) | 4147(1) | −3078(1) | 6206(1) | 23(1) |
| N(1) | 4880(1) | −936(2) | 8699(1) | 20(1) |
| N(2) | 6299(1) | −2243(2) | 8233(1) | 18(1) |
| O(1) | 4857(1) | −2226(2) | 9650(1) | 33(1) |
| O(2) | 6354(1) | −2710(2) | 9439(1) | 29(1) |
| P(1) | 5031(1) | 300(1) | 7523(1) | 14(1) |
| P(2) | 5933(1) | −1935(1) | 6759(1) | 12(1) |
| Pt(1) | 4685(1) | −1396(1) | 6874(1) | 12(1) |
| C(500) | 5866(2) | −5480(3) | 9494(2) | 32(1) |
| Cl(51) | 4907(1) | −5174(1) | 8943(1) | 47(1) |
| Cl(52) | 6558(1) | −5969(1) | 8958(1) | 50(1) |

EXAMPLES 1–8 (INVENTIVE)

Low Pressure Hydroformylations of 1-octene

The hydroformylation was carried out in parallel in 8 autoclaves of identical design. To this end, in a Schlenk tube, 1.8 mg (7.0 μmol) of rhodium dicarbonyl acetylacetonate were dissolved in 24 ml of toluene and admixed with 39 mg (0.14 mmol) of 6-phenylphosphino-1H-pyridin-2-one. The resulting solution was divided equally between the 8 autoclaves and then conditioned by stirring at 90° C. and under 5 bar of synthesis gas (CO/H=1:1) for 30 minutes. The temperature for the individual autoclaves was then adjusted as specified in table 3 and the pressure for all autoclaves was increased uniformly to 10 bar of CO/H$_2$ (1:1). Under these conditions, 0.69 g (6.2 mmol) of 1-octene per autoclave was added via a lock and each lock was subsequently flushed with 0.5 ml of toluene. Pressure and temperature were kept constant over the entire reaction time. After 4 hours of reaction time, the autoclaves were cooled, decompressed and emptied. The resulting reaction solutions were analyzed by gas chromatography (GC). The results obtained are reproduced in table 3.

TABLE 3

Hydroformylation of 1-octene at 10 bar of $CO/H_2$ and different temperatures

| Example | Temperature [° C.] | 1-Octene (conversion) [%] | Total nonanals (yield) [%] | n-fraction[a] (selectivity) [%] | α-fraction[b] (selectivity) [%] |
|---|---|---|---|---|---|
| 1 | 40 | 3 | 2 | 93 | 100 |
| 2 | 50 | 10 | 9 | 95 | 100 |
| 3 | 65 | 56 | 53 | 97 | 100 |
| 4 | 80 | 95 | 85 | 96 | 100 |
| 5 | 95 | 98 | 85 | 96 | 100 |
| 6 | 110 | 96 | 82 | 93 | 100 |
| 7 | 125 | 90 | 71 | 89 | 100 |
| 8 | 140 | 81 | 34 | 83 | 100 |

[a]Fraction of n-nonanal
[b]n-Nonanal + 2-methyloctanal

COMPARATIVE EXAMPLES 1–8

Low Pressure Hydroformylations of 1-octene

In a similar manner to examples 1–8, the hydroformylation was carried out in parallel in 8 autoclaves of identical design. To this end, in a Schlenk tube, 1.8 mg (7.0 μmol) of rhodium dicarbonyl acetylacetonate were dissolved in 24 ml of toluene and admixed with 37 mg (0.14 mmol) of triphenylphosphine. The resulting solution was divided equally between the 8 autoclaves and then conditioned by stirring at 90° C. and under bar of synthesis gas ($CO/H_2$=1:1) for 30 minutes. The temperature for the individual autoclaves was then adjusted as specified in table 4 and the pressure for all autoclaves was increased uniformly to 10 bar of $CO/H_2$ (1:1). Under these conditions, 0.69 g (6.2 mmol) of 1-octene per autoclave was added via a lock and each lock was subsequently flushed with 0.5 ml of toluene. Pressure and temperature were kept constant over the entire reaction time. After 4 hours of reaction time, the autoclaves were cooled, decompressed and emptied. The resulting reaction solutions were analyzed by gas chromatography (GC). The results obtained are reproduced in table 4.

TABLE 4

Hydroformylation of 1-octene with rhodium/triphenylphosphine as a catalyst at 10 bar of $CO/H_2$ and different temperatures

| Comparative example | Temperature [° C.] | 1-Octene (conversion) [%] | Total nonanals (yield) [%] | n-fraction[a] (selectivity) [%] | α-fraction[b] (selectivity) [%] |
|---|---|---|---|---|---|
| 1 | 40 | 16 | 4 | 77 | 100 |
| 2 | 50 | 17 | 6 | 76 | 100 |
| 3 | 65 | 22 | 22 | 72 | 100 |
| 4 | 80 | 98 | 89 | 73 | 100 |
| 5 | 95 | 98 | 84 | 70 | 98 |
| 6 | 110 | 99 | 67 | 61 | 94 |
| 7 | 125 | 97 | 44 | 56 | 93 |
| 8 | 140 | 94 | 12 | 62 | 97 |

[a]Fraction of n-nonanal
[b]n-Nonanal + 2-methyloctanal

General Experimental Description for Carrying Out Batchwise Hydroformylation Experiments (Examples 9–11)

Rhodium precursor, ligand and solvent were mixed in a Schlenk tube under nitrogen inert gas. The resulting solution was transferred to a 70 ml of 100 ml autoclave flushed with $CO/H_2$ (1:1). 5 bar of $CO/H_2$ (1:1) were injected at room temperature. Under vigorous stirring with a sparging stirrer, the reaction mixture was heated to the desired temperature within 30 minutes. A lock was then used to inject the olefin used into the autoclave using elevated $CO/H_2$ pressure. The desired reaction pressure was then set immediately by injecting $CO/H_2$ (1:1). During the reaction, the pressure was kept constant in the reactor using a pressure regulator. After the reaction time, the autoclave was cooled, decompressed and emptied. The reaction mixture was analyzed by means of gas chromatography.

EXAMPLE 9

Low Pressure Hydroformylation of 1-octene

Starting from 7.4 mg (29 μmol) of rhodium dicarbonyl acetylacetonate, 162 mg (0.58 mmol) of 6-diphenylphosphino-1H-pyridin-2-one, 25.6 g (228 mmol) of 1-octene and 25 g toluene, a 1-octene conversion of 100% was obtained in accordance with the general experimental procedure at 100° C. and 10 bar of $CO/H_2$ after 3 hours of reaction time. The yield of nonanals was 91%, the selectivity for n-nonanal (n-fraction) was 97% and the selectivity for n-nonanal and 2-methyloctanal (α-fraction) was 100%.

EXAMPLE 10

Low Pressure Hydroformylation of 2-octene

Starting from 7.3 mg (28 μmol) of rhodium dicarbonyl acetylacetonate, 162 mg (0.58 mmol) of 6-diphenylphosphino-1H-pyridin-2-one, 25.4 g (226 mmol) of 2-octene (cis:trans ratio=80:20) and 25 g toluene, a 2-octene conversion of 100% was obtained in accordance with the general experimental procedure at 90° C. and 10 bar of $CO/H_2$ after 3 hours of reaction time. The yield of nonanals was 95%, the selectivity for n-nonanal (n-fraction) was 5% and the selectivity for n-nonanal and 2-methyloctanal (α-fraction) was 57%.

EXAMPLE 11

Low Pressure Hydroformylation of 1-butene

Starting from 1.9 mg (7.4 μmol) of rhodium dicarbonyl acetylacetonate, 39 mg (0.14 mmol) of 6-diphenylphosphino-1H-pyridin-2-one, 6.5 g (37 mmol of 1-butene) of a mixture of 32% of 1-butene and 68% of isobutane, and 6.0 g of toluene, a 1-butene conversion of 100% was achieved in accordance with the general experimental procedure at 90° C. and total pressure 16 bar after a reaction time of 4 hours. The yield of aldehydes was 100% and the selectivity for n-valeraldehyde (n-fraction) 97%.

EXAMPLE 12

Hydroformylation of Functionalized Olefins According to Table 5 Using 6-diphenylphosphino-1H-pyridin-2-one (6-DPPon) as a Ligand 1.8 mg (6.98 µmol, 1 eq) of [Rh(CO)$_2$acac] were dissolved in 10 ml of toluene and admixed with 39.1 mg (0.14 mmol, 20 eq) of 6-diphenylphosphinopyridone. The orange-colored solution was stirred for 5 min and then admixed with 6.98 mmol (1 000 eq) of the particular substrate. The solution was transferred to the autoclave, 10 bar of CO/H$_2$ (1:1) were injected and the autoclave was heated to 70° C. After 20 h, the reaction was stopped by cooling to room temperature and decompressing the autoclave. The solution was filtered through a little silica gel together with approx. 50 ml of ethyl acetate and concentrated under reduced pressure. The crude products were analyzed by means of $^1$H and $^{13}$C NMR spectroscopy.

COMPARATIVE EXAMPLE 13

Hydroformylation of the Substrates in Accordance with Table 5 Using Triphenylphosphine as a Ligand 1.8 mg (6.98 µmol, 1 eq) of [Rh(CO)$_2$acac] (acac=acetylacetonate) were dissolved in 10 ml of toluene and admixed with 36.9 mg (0.14 mmol, 20 eq) of triphenylphosphine. The pale yellow solution was stirred for 5 min and then admixed with 6.98 mmol (1 000 eq) of the particular substrate. The solution was transferred to the autoclave, 10 bar of CO/H$_2$ (1:1) were injected and the autoclave was heated to 70° C. After 20 h, the reaction was stopped by cooling to room temperature and decompressing the autoclave. The solution was filtered through a little silica gel together with approx. 50 ml of ethyl acetate and concentrated under reduced pressure. The crude products were analyzed by means of $^1$H and $^{13}$C NMR spectroscopy.

TABLE 5[1]

| Substrate | 6-DPPon | | | TPP | | |
|---|---|---|---|---|---|---|
| | linear | branched | conversion | linear | branched | conversion |
|  | 95.4 | 4.6 | >99%[2],[3] | 89.6 | 10.4 | >99%[2],[3] |
|  | 89.0 | 11.0 | >99%[3] | 74.1 | 25.9 | >99%[3] |
|  | 96.0 | 4.0 | >99% | 77.0 | 23.0 | >99% |
|   addition of methanol* | 83.0 | 17.0 | >99% | 77.2 | 22.8 | >99% |
|   addition of 500 eq of AcOH* | 80.6 | 19.4 | >99% | — | — | — |
|  | 96.2 | 3.8 | >99% | 71.1 | 28.9 | >99% |
|  | 86.5 | 13.5 | >99% | 61.6 | 38.4 | >99% |
|  | 95.8 | 4.2 | >99% | 69.0 | 31.0 | >99% |
|  | 97.0 | 3.0 | >99% | 74.0 | 26.0 | >99% |
|  | 97.0 | 3.0 | >99% | 72.0 | 28.0 | not determined |

[1]The conversion and selectivity were determined by integrating the relevant signal groups in the $^1$H NMR spectrum
[2]Product mixtures in the isolation as a result of oligo- or polymerization
[3]The equilibrium is >90% on the side of the corresponding 5- or 6-membered lactols

EXAMPLE 14

Preparation of 6-(diphenylphosphino)-2-pivaloylaminopyridine [6-DPPAP]

When the formation of noncovalent bonds between the ligands is disrupted by adding acetic acid and methanol, the n-selectivity reduces at otherwise still good conversions.

14.1 Preparation of 6-bromo-2-aminopyridine

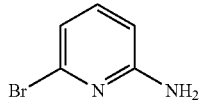

In a steel autoclave having a glass insert, 10.00 g of 2,6-dibromopyridine (42.2 mmol) were suspended in 50 ml of concentrated aqueous ammonia. The autoclave was closed and heated to 190° C. for 6 h in a heating mantle (pressurized to approx. 25 bar). After the cooling and decompression of the autoclave, the contents were admixed with 100 ml of ethyl acetate and the resulting phases were separated. The aqueous phase was extracted twice with 100 ml of ethyl acetate each time, the combined organic phases were dried over $Na_2SO_4$ and the solvent was removed under reduced pressure.

The residue was dissolved in 250 ml of cyclohexane/ethyl acetate (1:1) to remove 2,6-diaminopyridine which had formed, filtered together with a further 250 ml of cyclohexane/ethyl acetate (1:1) through a short silica gel column (5×20 cm), and freed of solvent under reduced pressure. Sublimation of the residue at 90° C. and $10^{-1}$ mbar afforded 6.49 g (37.5 mmol, 88.9%) of 6-bromo-2-aminopyridine as a white solid.

14.2 Electrophilic Route
14.2.1 Preparation of 6-bromo-2-pivaloylaminopyridine

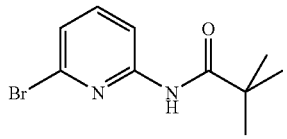

4.0 g (23.1 mmol) of 6-bromo-2-aminopyridine from example 14.1 were dissolved in 25 ml of dichloromethane and admixed with 4.1 ml (2.92 g, 28.9 mmol) of triethylamine. After cooling to 0° C., a solution of 3.1 ml (3.06 g, 25.4 mmol) of pivaloyl chloride in 5.0 ml of dichloromethane was added dropwise over a period of 10 min. The reaction mixture was allowed to warm to room temperature overnight and, for workup, poured onto 100 ml of dist. $H_2O$. The phases were separated, the aqueous phase was extracted twice with 100 ml each time of ethyl acetate and the combined organic phases were dried over $Na_2SO_4$. The solvent was removed under reduced pressure, and the residue was dissolved in dichloromethane and filtered through a short silica gel column (3×10 cm). After the solvent had been removed under reduced pressure, 5.73 g (22.3 mmol, 96.5%) of 6-bromo-2-pivaloylaminopyridine were obtained as a white solid.

14.2.2 Preparation of 6-(diphenylphosphino)-2-pivaloylaminopyridine [6-DPPAP]

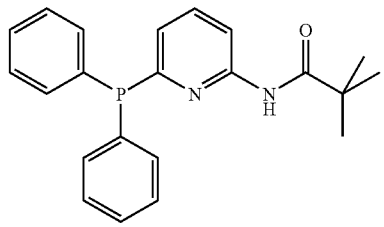

1.00 g (3.89 mmol) of 6-bromo-2-pivaloylaminopyridine from example 14.2.1 was dissolved in 10 ml of diethyl ether and admixed at 0° C. with 3.64 ml (8.00 mmol) of (iso-$C_3H_7$)MgBr (2.2M in $Et_2O$). The suspension was stirred at 0° C. for 18 h and then admixed with 0.7 ml (0.86 g, 3.89 mmol) of chlorodiphenylphosphine. The mixture was allowed to warm to ambient temperature overnight and was then hydrolyzed by adding 10 ml of dist. $H_2O$. The resulting phases were separated and the aqueous phase was extracted twice with 50 ml each time of ethyl acetate. The organic phases were combined and dried over $Na_2SO_4$, and the solvent was removed under reduced pressure. The residue was filtered together with dichloromethane through a short silica gel column (2×10 cm) and the solvent was removed under reduced pressure. The resulting oil was crystallized by digesting with petroleum ether/diethyl ether (40/60). The crystals were filtered off and washed with petroleum ether/diethyl ether (40/60). 0.38 g (1.05 mmol, 27.0%) of 6-(diphenylphosphino)-2-pivaloylaminopyridine was obtained as a solid.

$^{31}P$ NMR (121.5 MHz, $C_6D_6$): $\delta[ppm]=-3.9$ 14.3 Nucleophilic Route
14.3.1 Preparation of 6-(diphenylphosphino)-2-aminopyridine [6-DPAP]

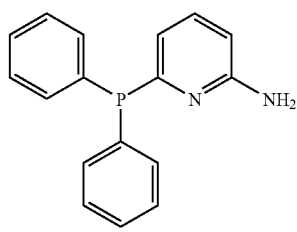

At −78° C., 200 ml of ammonia were condensed in and 5.00 g of sodium (216.8 mmol) were dissolved therein within 5 min. The resulting dark blue solution was admixed with 11.70 g of triphenylphosphine (108.4 mmol) in portions, stirred at −78° C. for approx. 2 h and then admixed with 15.00 g (86.7 mmol) of 6-bromo-2-aminopyridine from example 14.1. After 250 ml of toluene had been added, the cold bath was removed and the ammonia evaporated off overnight. The residue was hydrolyzed with 150 ml of dist. $H_2O$ and admixed with 150 ml of saturated NaCl solution, the resulting phases were separated and the aqueous phase was extracted once with 200 ml of toluene. The combined organic phases were dried over $MgSO_4$ and concentrated under reduced pressure. The product was purified by column chromatography (first with dichloromethane to remove diphenylphosphine, then with 9:1 dichloromethane/ethyl acetate). Resulting mixed fractions were purified by sublimation at 180° C. and 10⁻² mbar. 14.26 g (51.2 mmol, 59%) of 6-(diphenylphosphino)-2-aminopyridine were obtained as a white solid.

$^{31}$P NMR (121.5 MHz, C$_6$D$_6$): δ[ppm]=−3.7

14.3.2 Preparation of 6-(diphenylphosphino)-2-pivaloylaminopyridine

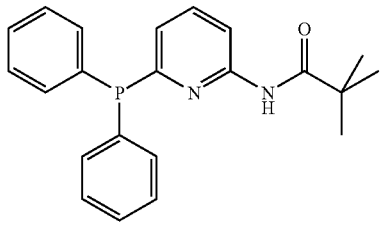

2.0 g (7.2 mmol) of 6-(diphenylphosphino)-2-aminopyridine from example 14.3.1 were dissolved in 40 ml of dichloromethane and admixed with 1.6 ml (1.2 g, 10.8 mmol) of triethylamine and 0.16 g (0.7 mmol) of 4-dimethylaminopyridine (DMAP). After cooling to 0° C. (H$_2$O/ice), 1.2 ml (1.2 g, 8.8 mmol) of pivaloyl chloride were slowly added dropwise and the mixture was kept at this temperature for 3 h. The mixture was allowed to warm to room temperature overnight and the solvent was then removed under reduced pressure. The residue was purified by filtration together with cyclohexane/ethyl acetate (1:1) through a short silica gel column (3×10 cm). The solvent was removed under reduced pressure and the resulting oil crystallized by digesting with petroleum ether (40/60). The solid was filtered off, washed with petroleum ether (40/60) and dried under reduced pressure. 2.25 g (6.2 mmol, 86.1%) of 6-(diphenylphosphino)-2-pivaloylaminopyridine were obtained as a beige-colored solid.

$^{31}$P NMR (121.5 MHz, C$_6$D$_6$): δ[ppm]=−3.9

FIG. 2 shows an ORTEP diagram of the determined crystal structure of 6-(diphenylphosphino)-2-pivaloylaminopyridine.

EXAMPLE 15

Preparation of 6-(diphenylphosphino)-2-acetylaminopyridine [6-DPAAP]

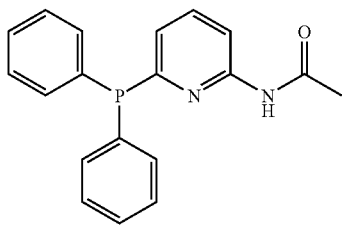

0.10 g (0.36 mmol) of 6-(diphenylphosphino)-2-aminopyridine from example 14.3.1 was dissolved in 2.0 ml of dichloromethane and admixed with 0.05 ml (0.04 g, 0.40 mmol) of triethylamine and a spatula-tip of DMAP. After 0.04 ml (0.04 g, 0.40 mmol) of acetic anhydride had been added, the mixture was stirred at room temperature for 2 h and then the solvent was removed under reduced pressure. The residue was purified by column chromatography with cyclohexane/ethyl acetate (1:1). 0.074 g (0.23 mmol, 63.9%) of 6-(diphenylphosphino)-2-acetylaminopyridine was obtained as a beige-colored solid.

$^{31}$P NMR (121.5 MHz, C$_6$D$_6$): δ[ppm]=−3.2

EXAMPLE 16

Preparation of 3-(diphenylphosphino)isoquinolin-1(2H)-one [3-DPICon]

16.1 Preparation of o-cyanomethylbenzoic acid

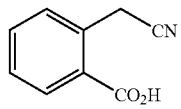

5.0 g (37.3 mmol) of phthalide and 5.0 g (76.8 mmol) of potassium cyanide, finely ground with a mortar and under vigorous stirring, were heated to 180° C. for 3.5 h in an open round-bottom flask. In the course of this, the melt darkened in color and had solidified after the reaction time. The solid was dissolved in 50 ml of dist. H$_2$O and the solution was extracted twice with 100 ml each time of ethyl acetate. The combined organic phases contain unconverted phthalide and were discarded. The aqueous phase was admixed with 5.0 g of FeSO$_4$.7H$_2$O in order to bind excess cyanide and acidified with concentrated HCl down to a pH of 2. The precipitated solid was filtered off with suction through a frit filled with kieselguhr and washed with ethyl acetate, and the filtrate was transferred to a separating funnel. After phase separation, the aqueous phase was extracted twice more with 100 ml each time of ethyl acetate, the combined organic phases were dried over MgSO$_4$ and the solvent was removed under reduced pressure. 5.34 g (33.1 mmol, 88.7%) of o-cyanomethylbenzoic acid were obtained and were used for the following reaction without further purification.

16.2 Preparation of 1,3-dichloroisoquinoline

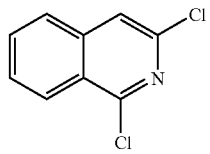

1.3 g (6.24 mmol) of phosphorus pentachloride were dissolved in 6 ml of phosphoryl chloride and admixed with 1.0 g (6.21 mmol) of o-cyanomethylbenzoic acid from example 16.1 in portions. After stirring at room temperature for 90 min, all had dissolved, and the solution was heated to 70° C. for 16 h. After the mixture had been cooled, it was poured cautiously onto 50 g of ice and admixed with 50 ml of ethyl acetate. The phases were separated and the aqueous phase was extracted twice with 50 ml each time of acetic acid. The combined organic phases were washed with 50 ml of H$_2$O and 50 ml of saturated NaHCO$_3$ solution, and dried over MgSO$_4$, and the solvent was removed under reduced pressure. The brown, crystalline crude product was purified by filtering together with dichloromethane/cyclohexane (1:1) through a short silica gel column (2×15 cm). 1.04 g (5.25 mmol, 84.5%) of 1,3-dichloroisoquinoline were obtained.

16.3 Preparation of 1-t-butoxy-3-chloroisoquinoline

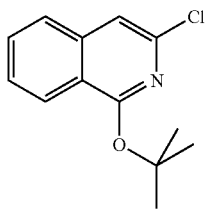

1.0 g (5.05 mmol) of 1,3-dichloroisoquinoline from example 16.2 was dissolved in 20 ml of dry toluene, admixed with 0.68 g (6.06 mmol) of potassium tert-butoxide and stirred at 80° C. for 3 h. After the mixture had been cooled, it was filtered together with 50 ml of dichloromethane through a short silica gel column (1×5 cm) and the solvent was removed under reduced pressure. 1.06 g (4.50 mmol, 89.1%) of 1-t-butoxy-3-chloroisoquinoline were obtained.

16.4 Preparation of 3-chloroisoquinolin-1(2H)-one

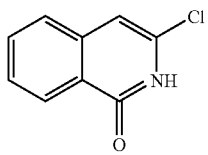

0.5 g (2.12 mmol) of 1-t-butoxy-3-chloroisoquinoline from example 16.3 was dissolved in 5.0 ml of formic acid and stirred at room temperature for 20 h. The solution was then diluted with 10 ml of $H_2O$, and the precipitated solid was filtered off through a glass frit, washed with 10 ml of $H_2O$/formic acid (2:1) and dried under high vacuum. 0.30 g (1.67 mmol, 78.8%) of 3-chloroisoquinolin-1(2H)-one was obtained. The combined aqueous phases were concentrated to dryness under reduced pressure and the resulting solid was purified by column chromatography (5:1 dichloromethane/ethyl acetate), whereupon a further 0.040 g (0.22 mmol, 10.4%) of 3-chloroisoquinolin-1(2H)-one was obtained.

16.5 Preparation of 3-(diphenylphosphino)isoquinolin-1(2H)-one [3-DPICon]

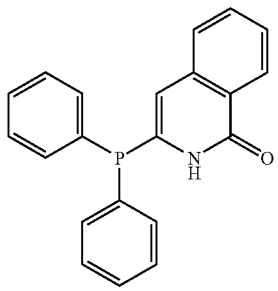

At −78° C., 130 ml of ammonia were condensed in and 2.10 g of sodium (91.3 mmol) were dissolved therein within 5 min. The dark blue solution was admixed with 11.70 g of triphenylphosphine (44.6 mmol) in portions and stirred at −78° C. for 2 h. After 100 ml of dry tetrahydrofuran had been added, the cold bath was removed and the ammonia evaporated off within 2 h. After the orange-colored solution had been warmed to room temperature, it was admixed with 4.0 g (22.3 mmol) of 3-chloroisoquinolin-1(2H)-one from example 16.4 in portions and heated to 60° C. for 20 h. After the mixture had been cooled, it was admixed with 50 ml of dist. $H_2O$, and the aqueous phase was extracted three times with 100 ml each time of dichloromethane, and the combined organic phases were dried over $MgSO_4$ and concentrated under reduced pressure. The resulting solid was digested with dichloromethane, filtered off and dried. The filtrate was concentrated and the resulting solid again digested with dichloromethane, filtered off and dried. The solids were combined. 4.47 g (13.6 mmol, 60.9%) of 3-(diphenyl-phosphino)isoquinolin-1(2H)-one were obtained. The filtrate was concentrated under reduced pressure and the resulting solid purified by column chromatography (5:1 dichloromethane/ethyl acetate). A further 0.216 g (0.66 mmol, 2.9%) of 3-(diphenylphosphino)isoquinolin-1(2H)-one was obtained.

$^{31}P$ NMR (121.5 MHz, $C_6D_6$): δ[ppm]=−8.7

FIG. 3 shows an ORTEP diagram of the determined crystal structure of 3-(diphenyl-phosphino)isoquinolin-1(2H)-one.

EXAMPLE 17

Preparation of 2-diphenylphosphinopyridine [2-DPP]

The synthesis was effected to the method described in similarly J. Am. Chem. Soc. 1984, 106(5), 1323–32.

EXAMPLE 18

Crystal Structure Analysis of [cis-$PtCl_2$(6-DPPAP)(3-DPICon)($H_2O$)]

A Schlenk tube was initially charged with 37.4 mg (100 μmol) of [cis-$PtCl_2$(COD)], 36.2 mg (100 μmol) of 6-(diphenylphosphino)-2-pivaloylaminopyridine and 32.9 mg (100 μmol) of 3-(diphenylphosphino)isoquinolin-1(2H)-one, which were admixed with 4.0 ml of toluene and dissolved by heating to approx. 80° C. In the course of cooling, the platinum complex precipitated out as a white solid. The toluene was decanted off, the residue was washed twice with 3 ml each time of pentane and the white solid was dried under high vacuum. Suitable crystals for a crystal structure analysis were obtained from a solution of 10 mg of [cis-$PtCl_2$(6-DPPAP)(3-DPICon)($H_2O$)] in 1.0 ml of toluene.

FIG. 4 shows an ORTEP diagram of the determined crystal structure.

EXAMPLE 19

Hydroformylation of 1-octene 1.8 mg (6.98 μmol) of [Rh(CO)$_2$acac] were dissolved in 10 ml of toluene and admixed with 0.14 mmol of the particular ligand or their 1:1 mixture (heterodimers). The solution was stirred for 5 min, gently heated if necessary for complete dissolution and then admixed with 1.1 ml (0.78 g, 6.98 mmol) of 1-octene. The solution was transferred to the autoclave, 10 bar of CO/$H_2$ (1:1) were injected and the autoclave was heated to 70° C. After 20 h, the reaction was stopped by cooling to room temperature and decompressing the autoclave. The autoclave effluent was analyzed by GC and $^1H$ NMR spectroscopy.

| Ligand(s) | Linear:branched ratio | Conversion [%] |
|---|---|---|
| 2-DPP/3-DPICon | 87:13 | quantitative |
| 2-DPAAP/3-DPICon | 95:5 | quantitative |
| 2-DPPAP/3-DPICon | 94:6 | quantitative |

EXAMPLE 20

Hydroformylation of Different Substrates Using 2-DPPAP/3-DPICon 1.8 mg (6.98 µmol) of [Rh(CO)$_2$acac] were dissolved in 10 ml of toluene and admixed with 0.14 mmol of the two ligands (1:1 mixture). The solution was stirred for 5 min, gently heated if necessary for complete dissolution and then admixed with 6.98 mmol of the particular substrate. The solution was transferred to the autoclave, 10 bar of CO/H$_2$ (1:1) were injected and the autoclave was heated to 70° C. After 20 h, the reaction was stopped by cooling to room temperature and decompressing the autoclave. The solution was filtered through a little silica gel together with approx. 50 ml of ethyl acetate and concentrated under reduced pressure. The crude products were analyzed by means of $^1$H and $^{13}$C NMR spectroscopy.

| Substrate | Linear:branched ratio | Conversion [%] |
|---|---|---|
| 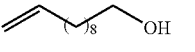 | 95:5 | quantitative |
| 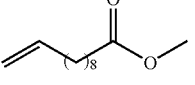 | 94:6 | quantitative |
| 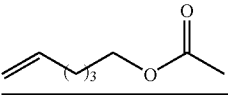 | 93:7 | quantitative |

EXAMPLE 21

Quantum Chemistry Calculations

Method: B-P86/SV(P)

| Ligand 1 | Ligand 2 | Stable dimer | P—P distance [Å] |
|---|---|---|---|
| 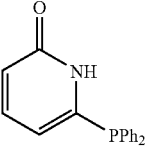 | 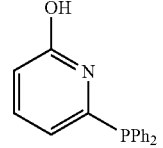 | yes | 3.75 |
| 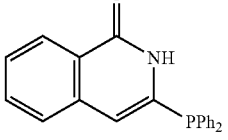 | 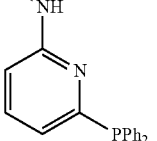 | yes | 3.77 |
| 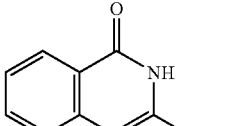 | 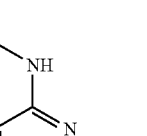 | yes | 3.81 |
| 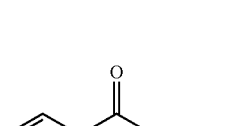 | 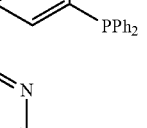 | yes | 3.82 |

We claim:

1. A process for hydroformylating compounds which contain at least one ethylenically unsaturated double bond by reacting with carbon monoxide and hydrogen in the presence of a catalyst comprising at least one complex of a metal of transition group VIII of the Periodic Table of the Elements with ligands which each have a phosphorus group and at least one functional group which is capable of forming intermolecular noncovalent bonds, wherein the complex has ligands which are dimerized via intermolecular noncovalent bonds and wherein the distance between the phosphorus atoms of the dimerized ligands is at most 5 Å.

2. A process as claimed in claim 1, wherein the distance between the phosphorus atoms of the dimerized ligands is in the range from 2.5 to 4.5 Å.

3. A process as claimed in claim 1, wherein the functional groups which are capable of forming intermolecular noncovalent bonds are selected from hydroxyl, primary, secondary and tertiary amino, thiol, keto, thioketone, imine, carboxylic ester, carboxamide, amidine, urethane, urea, sulfoxide, sulfoximine, sulfonamide and sulfonic ester groups.

4. A process as claimed in claim 1, wherein the functional groups which are capable of forming intermolecular noncovalent bonds are selected from groups which are capable of tautomerizing.

5. A process for hydroformylating compounds which contain at least one ethylenically unsaturated double bond by reacting with carbon monoxide and hydrogen in the presence of a catalyst comprising at least one complex of a metal of transition group VIII of the Periodic Table of the Elements with ligands which each have a phosphorus group and at least one functional group which is capable of forming intermolecular noncovalent bonds, wherein the complex has ligands which are dimerized via intermolecular noncovalent bonds and wherein the distance between the phosphorus atoms of the dimerized ligands is at most 5 Å, and wherein the ligands include at least one structural element of the general formulae I.a or I.b

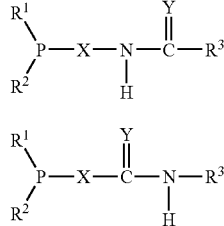 (I.a)

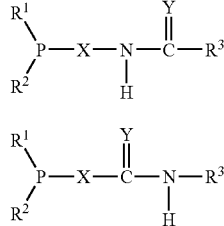 (I.b)

or tautomers thereof where

R¹ and R² are each independently alkyl, alkoxy, cycloalkyl, cycloalkoxy, heterocycloalkyl, heterocycloalkoxy, aryl, aryloxy, hetaryl or hetaryloxy, R³ is hydrogen or is as defined for R¹ and R², X is a bivalent bridging group having from 1 to 5 bridging atoms between the flanking bonds, Y is O, S or NR⁴, where R⁴ is hydrogen, alkyl, cycloalkyl, heterocycloalkyl, aryl or hetaryl, and two or more than two of the X radicals and R¹ to R⁴ together with the structural element of the formula I.a or I.b to which they are bonded may be a mono- or polycyclic compound.

6. A process as claimed in claim 5, wherein R¹ and R² in the ligands I.a or I.b, together with the phosphorus atom to which they are bonded, are each a 5- to 8-membered heterocycle which may optionally additionally be singly, doubly or triply fused with cycloalkyl, heterocycloalkyl, aryl or hetaryl, and the heterocycle and, where present, the fused groups may each independently bear one, two, three or four substituents which are selected from alkyl, cycloalkyl, heterocycloalkyl, aryl, hetaryl, COOR$^c$, COO⁻M⁺, SO₃R$^c$, SO₃⁻M⁺,PO₃(R$^c$)(R$^d$), (PO₃)²⁻(M⁺)₂, NE⁴E⁵, (NE⁴E⁵E⁶)⁺X⁻, OR$^e$, SR$^e$, (CHR$^f$CH₂O)$_y$R$^e$, (CH₂NE⁴)$_y$R$^e$, (CH₂CH₂NE⁴)$_y$R$^e$, halogen, nitro, acyl and cyano, where R$^c$ and R$^d$ are each identical or different radicals selected from alkyl, cycloalkyl, aryl and hetaryl, R$^e$, E⁴, E⁵, E⁶ are each identical or different radicals selected from hydrogen, alkyl, cycloalkyl, acyl, aryl and hetaryl, R$^f$ is hydrogen, methyl or ethyl, M⁺ is one cation equivalent, X⁻ is one anion equivalent and y is an integer from 1 to 240.

7. A process for hydroformylating compounds which contain at least one ethylenically unsaturated double bond by reacting with carbon monoxide and hydrogen in the presence of a catalyst comprising at least one complex of a metal of transition group VIII of the Periodic Table of the Elements with ligands which each have a phosphorus group and at least one functional group which is capable of forming intermolecular noncovalent bonds, wherein the complex has ligands which are dimerized via intermolecular noncovalent bonds and wherein the distance between the phosphorus atoms of the dimerized ligands is at most 5 Å, and wherein the ligands are selected from compounds of the general formulae I.1 to I.3

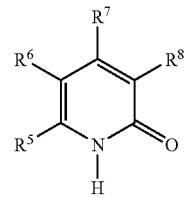 (I.1)

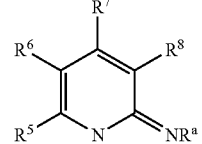 (I.2)

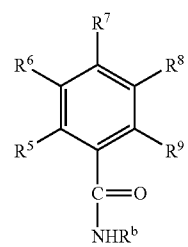 (I.3)

and the tautomers thereof where one of the R⁵ to R⁹ radicals is a group of the formula —W'—PR¹R² where W' is a single bond, a heteroatom, a heteroatom-containing group or a bivalent bridging group having from 1 to 4 bridging atoms between the flanking bonds, R¹ and R² are each independently alkyl, alkoxy, cycloalkyl, cycloalkoxy, heterocycloalkyl, heterocycloalkoxy, aryl, aryloxy, hetaryl or hetaryloxy, the R⁵ to R⁹ radicals which are not —W'—PR¹R² are each independently hydrogen, alkyl, cycloalkyl, heterocycloalkyl, aryl, hetaryl, WCOOR$^o$, WCOO⁻M⁺, W(SO₃)R$^o$, W(SO₃)⁻M⁺, WPO₃(R$^o$)(R$^p$), W(PO₃)²⁻(M⁺)₂, WNE¹E², W(NE¹E²E³)⁺X⁻, WOR$^q$, WSR$^q$, (CHR$^r$CH₂O)$_x$R$^q$, (CH₂NE¹)$_x$R$^q$, (CH₂CH₂NE¹)$_x$R$^q$, halogen, nitro, acyl or cyano, where W is a single bond, a heteroatom, a heteroatom-containing group or a bivalent bridging group having from 1 to 20 bridging atoms, R$^o$ and R$^p$ are each identical or different radicals selected from alkyl, cycloalkyl, aryl and hetaryl, R$^q$, E¹, E², E³ are each identical or different radicals selected from hydrogen, alkyl, cycloalkyl, acyl, aryl and hetaryl, R$^r$ is hydrogen, methyl or ethyl, M⁺ is one cation equivalent, X⁻ is one anion equivalent and x is an integer from 1 to 240, and in each case two adjacent R⁵, R⁶, R⁷, R⁸ and R⁹ radicals, together with the ring carbon atoms to which they are bonded, may also be a fused ring system having 1, 2 or 3 further rings, and R$^a$ and R$^b$ are each hydrogen, alkyl, acyl, cycloalkyl, heterocycloalkyl, aryl or hetaryl.

8. A process for hydroformylating compounds which contain at least one ethylenically unsaturated double bond by reacting with carbon monoxide and hydrogen in the presence of a catalyst comprising at least one complex of a metal of transition group VIII of the Periodic Table of the Elements with ligands which are selected from compounds of the general formulae I.1 to I.3

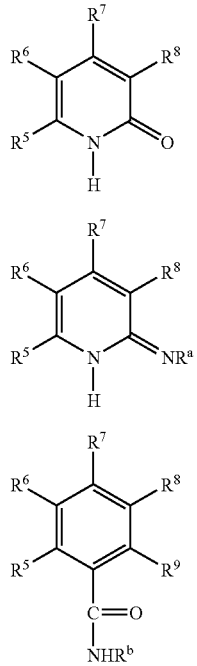

and the tautomers thereof where
one of the $R^5$ to $R^9$ radicals is a group of the formula —W'—$PR^1R^2$ where
W' is a single bond, a heteroatom, a heteroatom-containing group or a bivalent bridging group having from 1 to 4 bridging atoms between the flanking bonds,
$R^1$ and $R^2$ are each independently alkyl, alkoxy, cycloalkyl, cycloalkoxy, heterocycloalkyl, heterocycloalkoxy, aryl, aryloxy, hetaryl or hetaryloxy,
the $R^5$ to $R^9$ radicals which are not —W'—$PR^1R^2$ are each independently hydrogen, alkyl, cycloalkyl, heterocycloalkyl, aryl, hetaryl, $WCOOR^o$, $WCOO^-M^+$, $W(SO_3)R^o$, $W(SO_3)^-M^+$, $WPO_3(R^o)(R^p)$, $W(PO_3)^{2-}(M^+)_2$, $WNE^1E^2$, $W(NE^1E^2E^3)^+X^-$, $WOR^q$, $WSR^q$, $(CHR^rCH_2O)_xR^q$, $(CH_2NE^1)_xR^q$, $(CH_2CH_2NE^1)_xR^q$, halogen, nitro, acyl or cyano,
where
W is a single bond, a heteroatom, a heteroatom-containing group or a bivalent bridging group having from 1 to 20 bridging atoms,
$R^o$ and $R^p$ are each identical or different radicals selected from alkyl, cycloalkyl, aryl and hetaryl,
$R^q$, $E^1$, $E^2$, $E^3$ are each identical or different radicals selected from hydrogen, alkyl, cycloalkyl, acyl, aryl and hetaryl,
$R^r$ is hydrogen, methyl or ethyl,
$M^+$ is one cation equivalent,
$X^-$ is one anion equivalent and
x is an integer from 1 to 240,
and in each case two adjacent $R^5$, $R^6$, R7, $R^8$ and $R^9$ radicals, together with the ring carbon atoms to which they are bonded, may also be a fused ring system having 1, 2 or 3 further rings, and $R^a$ and $R^b$ are each hydrogen, alkyl, acyl, cycloalkyl, heterocycloalkyl, aryl or hetaryl.

9. A process as claimed in claim 6, wherein the ligands are selected from compounds of the general formulae I.i to I.iii

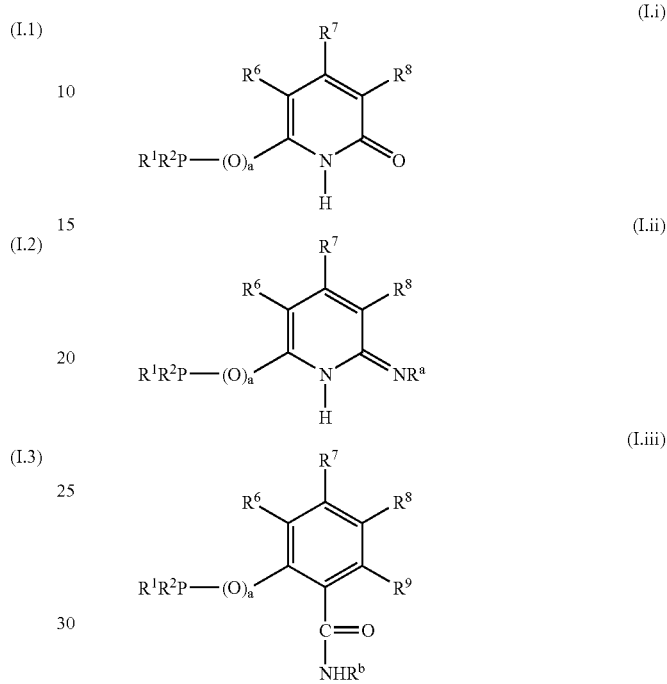

and the tautomers thereof where
a is 0 or 1,
$R^1$ and $R^2$ are each as defined above,
$R^6$ to $R^9$ are each independently hydrogen, $C_1$–$C_4$-alkyl, $C_1$–$C_4$-alkoxy, acyl, aryl, heteroaryl, halogen, $C_1$–$C_4$-alkoxycarbonyl or carboxylate,
and in each case two adjacent $R^6$, $R^7$, $R^8$ and $R^9$ radicals, together with the ring carbon atoms to which they are bonded, may also be a fused ring system having 1, 2 or 3 further rings, and
$R^a$ and $R^b$ are each hydrogen, alkyl, acyl, cycloalkyl or aryl.

10. A process as claimed in claim 8, wherein the ligands used comprise at least one compound of the formulae (1) to (4)

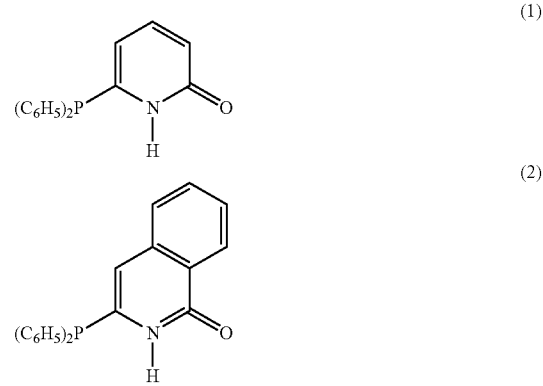

-continued

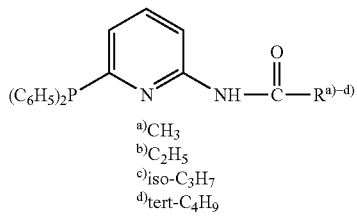

(3)

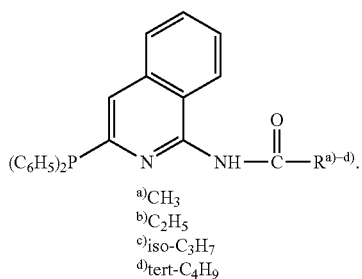

(4)

11. A process as claimed in claim 8, wherein the ligand used is one of the following ligands/ligand pairs (5) to (8):

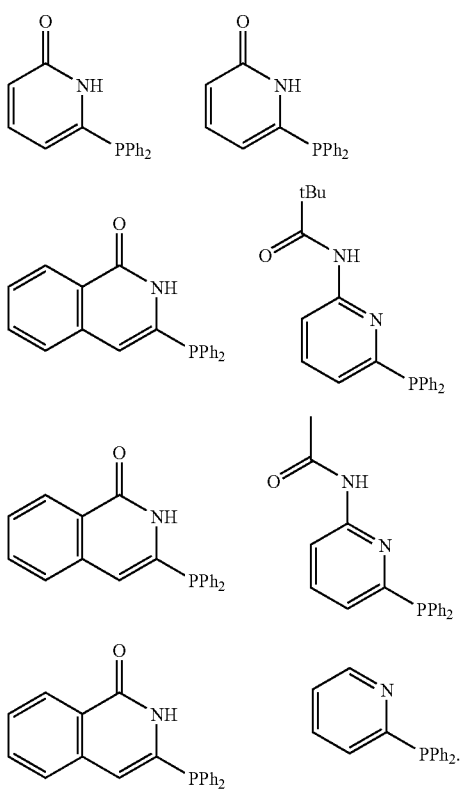

12. A catalyst as defined in claim 1.

13. A catalyst as claimed in claim 12, wherein the metal is selected from cobalt, nickel, rhodium, ruthenium and iridium.

14. A process as claimed in claim 2, wherein the distance is in the range from 3.5 to 4.2 Å.

15. A process as claimed in claim 2, wherein the distance is in the range from 3.6 to 4.1 Å.

16. A process as claimed in claim 7, wherein $R^1$ and $R^2$, together with the phosphorus atom to which they are bonded, are each a 5- to 8-membered heterocycle which may optionally additionally be singly, doubly or triply fused with cycloalkyl, heterocycloalkyl, aryl or hetaryl, and the heterocycle and, where present, the fused groups may each independently bear one, two, three or four substituents which are selected from alkyl, cycloalkyl, heterocycloalkyl, aryl, hetaryl, $COOR^c$, $COO^-M^+$, $(SO_3)R^c$, $(SO_3)^-M^+$, $PO_3(R^c)(R^d)$, $(PO_3)^{2-}(M^+)_2$, $NE^4E^5$, $(NE^4E^5E^6)^+X^-$, $OR^e$, $SR^e$, $(CHR^fCH_2O)_yR^e$, $(CH_2NE^4)_yR^e$, $(CH_2CH_2NE^4)_yR^e$, halogen, nitro, acyl and cyano, where $R^c$ and $R^d$ are each identical or different radicals selected from alkyl, cycloalkyl, aryl and hetaryl, $R^e$, $E^4$, $E^5$, $E^6$ are each identical or different radicals selected from hydrogen, alkyl, cycloalkyl, acyl, aryl and hetaryl, $R^f$ is hydrogen, methyl or ethyl, $M^+$ is one cation equivalent, $X^-$ is one anion equivalent and x is an integer from 1 to 240.

17. A process as claimed in claim 8, wherein $R^1$ and $R^2$, together with the phosphorus atom to which they are bonded, are each a 5- to 8-membered heterocycle which may optionally additionally be singly, doubly or triply fused with cycloalkyl, heterocycloalkyl, aryl or hetaryl, and the heterocycle and, where present, the fused groups may each independently bear one, two, three or four substituents which are selected from alkyl, cycloalkyl, heterocycloalkyl, aryl, hetaryl, $COOR^c$, $COO^-M^+$, $(SO_3)R^c$, $(SO_3)^-M^+$, $PO_3(R^c)(R^d)$, $(PO_3)^{2-}(M^+)_2$, $NE^4E^5$, $(NE^4E^5E^6)^+X^-$, $OR^e$, $SR^e$, $(CHR^fCH_2O)_yR^e$, $(CH_2NE^4)_yR^e$, $(CH_2CH_2NE^4)_yR^e$, halogen, nitro, acyl and cyano, where $R^c$ and $R^d$ are each identical or different radicals selected from alkyl, cycloalkyl, aryl and hetaryl, $R^e$, $E^4$, $E^5$, $E^6$ are each identical or different radicals selected from hydrogen, alkyl, cycloalkyl, acyl, aryl and hetaryl, $R^f$ is hydrogen, methyl or ethyl, $M^+$ is one cation equivalent, $X^-$ is one anion equivalent and y is an integer from 1 to 240.

* * * * *